US008088822B2

(12) United States Patent
Zhang et al.

(10) Patent No.: US 8,088,822 B2
(45) Date of Patent: Jan. 3, 2012

(54) USE OF FENRETINIDE OR BIOACTIVE DERIVATIVES THEREOF AND PHARMACEUTICAL COMPOSITIONS COMPRISING THE SAME

(75) Inventors: Ji Zhang, Rockville, MD (US); KanKan Wang, Shanghai (CN)

(73) Assignees: Ji Zhang, Rockville, MD (US); KanKan Wang, Shanghai (CN)

( * ) Notice: Subject to any disclaimer, the term of this patent is extended or adjusted under 35 U.S.C. 154(b) by 670 days.

(21) Appl. No.: 12/169,532

(22) Filed: Jul. 8, 2008

(65) Prior Publication Data
US 2010/0008896 A1    Jan. 14, 2010

(51) Int. Cl.
*A61K 31/28* (2006.01)
*A61K 31/16* (2006.01)

(52) U.S. Cl. .................................. 514/492; 514/613
(58) Field of Classification Search .................. 514/492, 514/613
See application file for complete search history.

(56) References Cited

U.S. PATENT DOCUMENTS

| | | | |
|---|---|---|---|
| 4,190,594 A | 2/1980 | Gander et al. | |
| 4,665,098 A | 5/1987 | Gibbs et al. | |
| 5,464,870 A | 11/1995 | Veronesi et al. | |
| 6,352,844 B1 | 3/2002 | Maurer et al. | |
| 6,368,831 B1 | 4/2002 | Maurer et al. | |
| 6,733,743 B2 | 5/2004 | Jordan | |
| 6,869,795 B1 | 3/2005 | Bartelmez et al. | |
| 7,169,813 B2 | 1/2007 | Formelli | |
| 7,169,819 B2 | 1/2007 | Gupta et al. | |
| 7,435,755 B2 * | 10/2008 | Konopleva et al. | 514/510 |

OTHER PUBLICATIONS

Ahn, S.G., et al., "Redox regulation of mammalian heat shock factor 1 is essential for Hsp gene activation and protection from stress," *Genes Dev.*, 2003, pp. 516-528, vol. 17.
Bello, R.I., et al., "Dicoumarol relieves serum withdrawal-induced $G_{0/1}$ blockade in HL-60 cells through a superoxide-dependent mechanism," *Biochem. Pharmacol.*, 2005, pp. 1613-1625, vol. 69.
Blanpain, C., et al., "Self-renewal, multipotency, and the existence of two cell populations within an epithelial stem cell niche," *Cell*, 2004, pp. 635-648, vol. 118.
Bonnet, D. & Dick, J.E., "Human acute myeloid leukemia is organized as a hierarchy that originates from a primitive hematopoietic cell," *Nat. Med.*, 1997, pp. 730-737, vol. 3.
Cobaleda, C., et al., "A primitive hematopoietic cell is the target for the leukemic transformation in human Philadelphia-positive acute lymphoblastic leukemia," *Blood*, 2000, pp. 1007-1013, vol. 95, No. 3.
D'Autréaux, B. & Toledano, M.B., "ROS as signalling molecules: mechanisms that generate specificity in ROS homeostasis," *Nature Reviews: Mol. Cell Biol.*, 2007, pp. 813-824, vol. 8.
Deininger, M.W.N., et al., "The molecular biology of chronic myeloid leukemia," *Blood*, 2000, pp. 3343-3356, vol. 96, No. 10.

Druker, B.J., et al., "Five-year follow-up of patients receiving imatinib for chronic myeloid leukemia," *N. Engl. J. Med.*, 2006, pp. 2408-2417, vol. 355, No. 23.
Graham, S.M., et al., "Primitive, quiescent, Philadelphia-positive stem cells from patients with chronic myeloid leukemia are insensitive to STI571 in vitro," *Blood*, 2002, pp. 319-325, vol. 99, No. 1.
Guan, Y., et al., "Detection, isolation, and stimulation of quiescent primitive leukemic progenitor cells from patients with acute myeloid leukemia (AML)," *Blood*, 2003, pp. 3142-3149, vol. 101, No. 8.
Guan, Y., & Hogge, D.E., "Proliferative status of primitive hematopoietic progenitors from patients with acute myelogenous leukemia (AML)," *Leukemia*, 2000, pp. 2135-2141, vol. 14.
Guzman, M.L., et al., "Preferential induction of apoptosis for primary human leukemic stem cells," *Proc. Natl. Acad. Sci. U.S.A.*, 2002, pp. 16220-16225, vol. 99, No. 25.
Hayashida, N., et al., "A novel HSF1-mediated death pathway that is suppressed by heat shock proteins," *EMBO J.*, 2006, pp. 4773-4783, vol. 25, No. 20.
Hope, K.J., et al., "Acute myeloid leukemia originates from a hierarchy of leukemic stem cell classes that differ in self-renewal capacity," *Nat. Immunol.*, 2004, pp. 738-743, vol. 5, No. 7.
Huntly, B.J. & Gilliland, D.G., "Blasts from the past: new lessons in stem cell biology from chronic myelogenous leukemia," *Cancer Cell*, 2004, pp. 199-201, vol. 6.
Jaiswal, A.K., "Nrf2 signaling in coordinated activation of antioxidant gene expression," *Free Radic. Biol. Med.*, 2004, pp. 1199-1207, vol. 36, No. 10.
Jordan, C.T., et al., "Cancer stem cells," *N. Engl. J. Med.*, 2006, pp. 1253-1261, vol. 355, No. 12.
Lapidot, T., et al., "A cell initiating human acute myeloid leukaemia after transplantation into SCID mice," *Nature*, 1994, pp. 645-648, vol. 367. Lynas, J.F., et al., "Inhibitors of the chymotrypsin-like activity of proteasome based on di- and tri-peptidyl α-keto aldehydes (glyoxals)," *Bioorganic & Medicinal Chemistry Letters*, 1998, pp. 373-378, vol. 8.
Meusser, B., et al., "ERAD: The long road to destruction," *Nat. Cell Biol.*, 2005, pp. 766-772, vol. 7, No. 8.
Murray, J.I., et al., "Diverse and specific gene expression responses to stresses in cultured human cells," *Mol. Biol. Cell*, 2004, pp. 2361-2374, vol. 15.

(Continued)

*Primary Examiner* — Raymond Henley, III
(74) *Attorney, Agent, or Firm* — Saliwanchik, Lloyd & Eisenschenk

(57) ABSTRACT

The present invention relates to a new medical use of fenretinide or bioactive derivatives thereof, particularly to the use of fenretinide or bioactive derivatives thereof in the preparation of a medicament for eliminating or killing tumor stem cells in a subject or for treating and/or preventing a tumor disease originating from tumor stem cells in a subject. The invention further relates to a new use of fenretinide or bioactive derivatives thereof in combination with other anti-tumor agents, a pharmaceutical composition comprising said fenretinide or bioactive derivatives thereof and at least one additional anti-tumor agent, a method of screening said other anti-tumor agent, a method of eliminating or killing tumor stem cells or particularly hematologic tumor stem cells in a subject by administrating said fenretinide or bioactive derivatives thereof, as well as a method of eliminating or killing tumor stem cells and tumor cells derived from tumor stem cells, particularly hematologic tumor stem cells and hematologic tumor cells derived from hematologic tumor stem cells in a subject by administrating said fenretinide or bioactive derivatives thereof in combination with other anti-tumor agent(s).

22 Claims, 24 Drawing Sheets

OTHER PUBLICATIONS

Oridate, N., et al., "Involvement of reactive oxygen species in N-(4-hydroxyphenyl)retinamide-induced apoptosis in cervical carcinoma cells," *J. Natl. Cancer Inst.*, 1997, pp. 1191-1198, vol. 89.

Shah, N.P., et al., "Multiple BCR-ABL kinase domain mutations confer polyclonal resistance to the tyrosine kinase inhibitor imatinib (STI571) in chronic phase and blast crisis chronic myeloid leukemia," *Cancer Cell*, pp. 117-125, vol. 2.

Sun, S.-Y., et al., "Mediation of N-(4-hydoxyphenyl)retinamide-induced apoptosis in human cancer cells by different mechanisms," *Cancer Res.*, 1999, pp. 2493-2498, vol. 59.

Xiao, L., et al., "Component plane presentation integrated self-organizing map for microarray data analysis," *FEBS Lett.*, 2003, pp. 117-124, vol. 538.

Zheng, P.Z., et al., "Systems analysis of transcriptome and proteome in retinoic acid/arsenic trioxide-induced cell differentiation/apoptosis of promyelocytic leukemia," *Proc. Natl. Acad. Sci. U.S.A.*, 2005, pp. 7653-7658, vol. 102, No. 21.

* cited by examiner

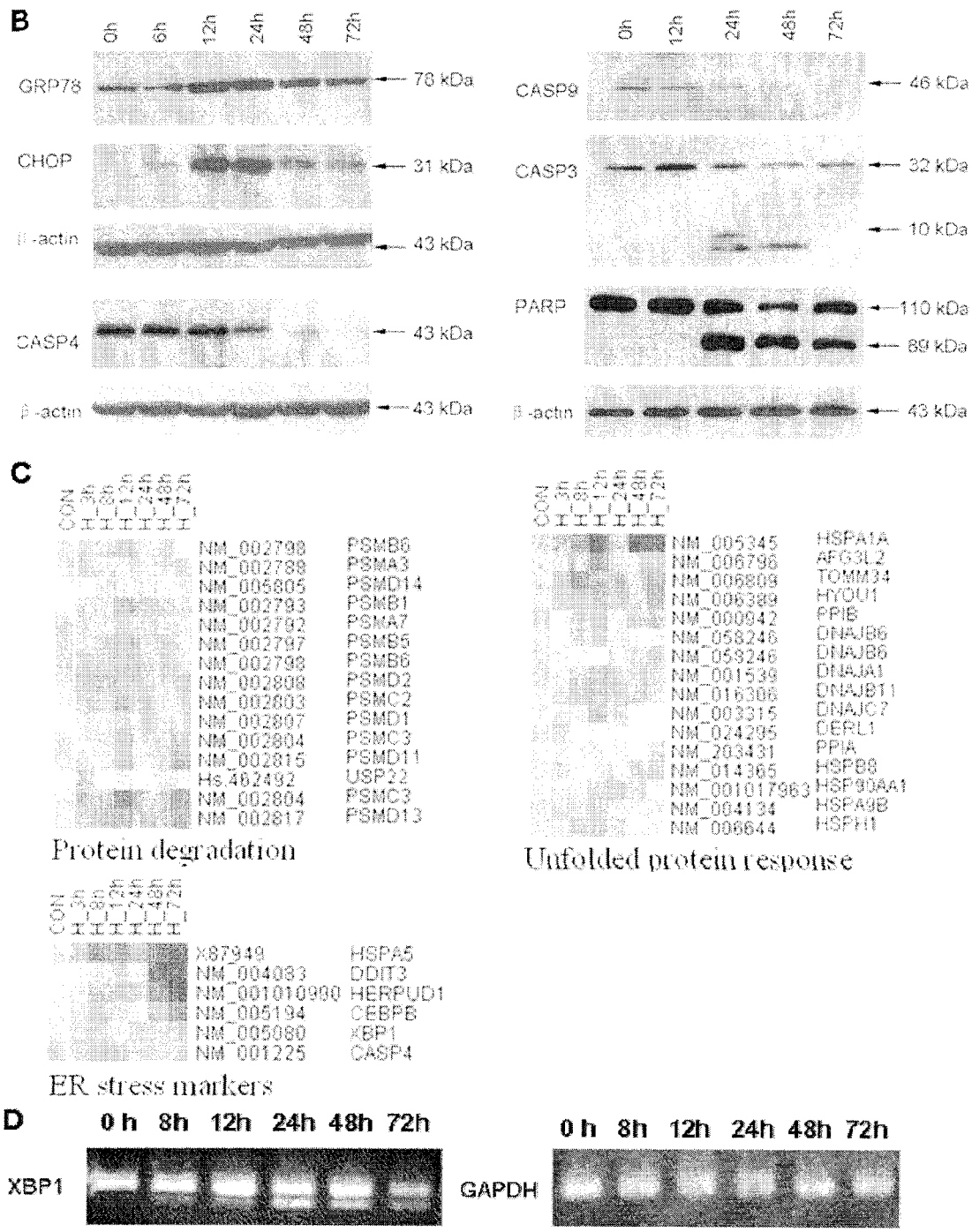
FIG. 7 (B-D)

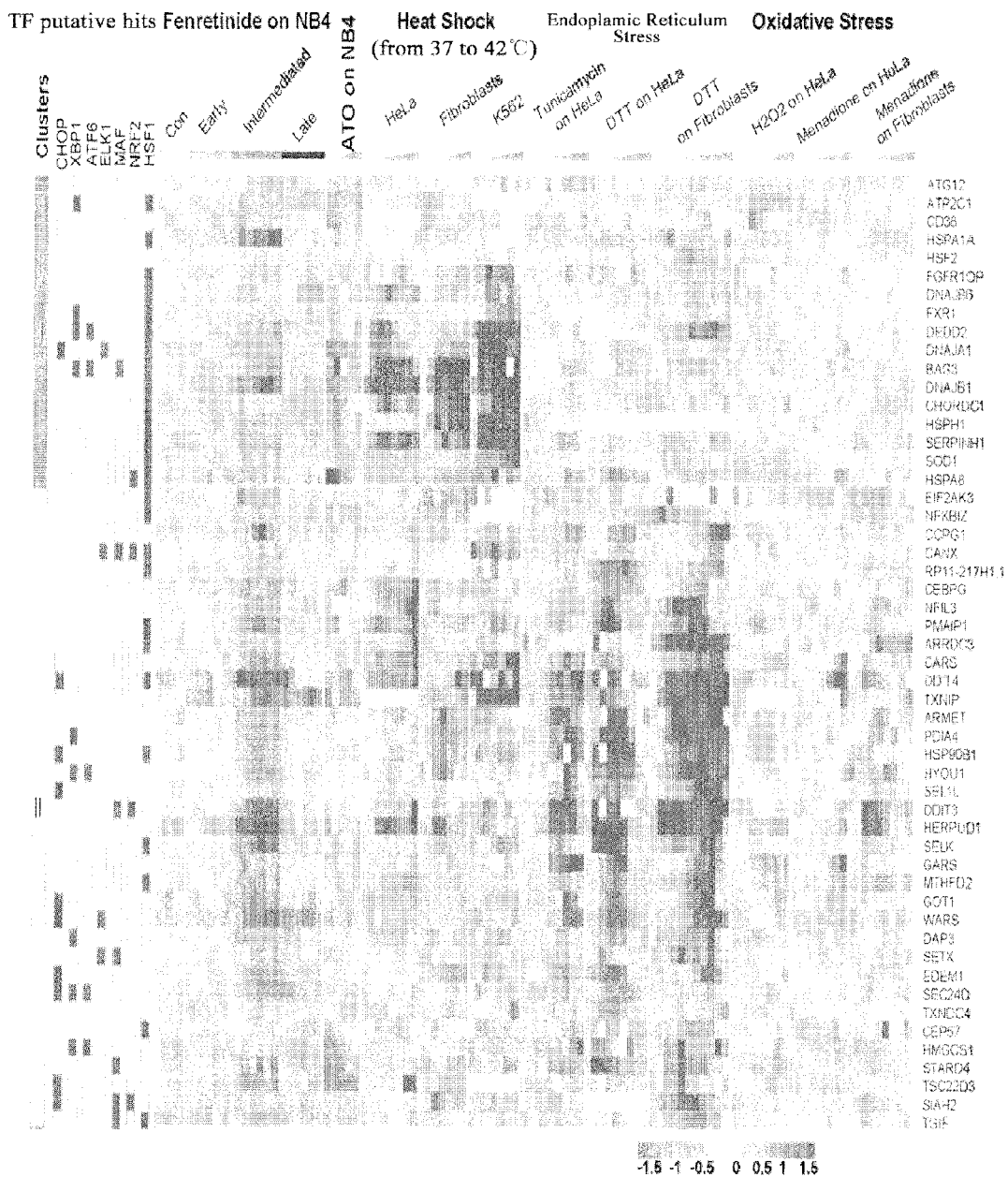
FIG. 9 (to be continued)

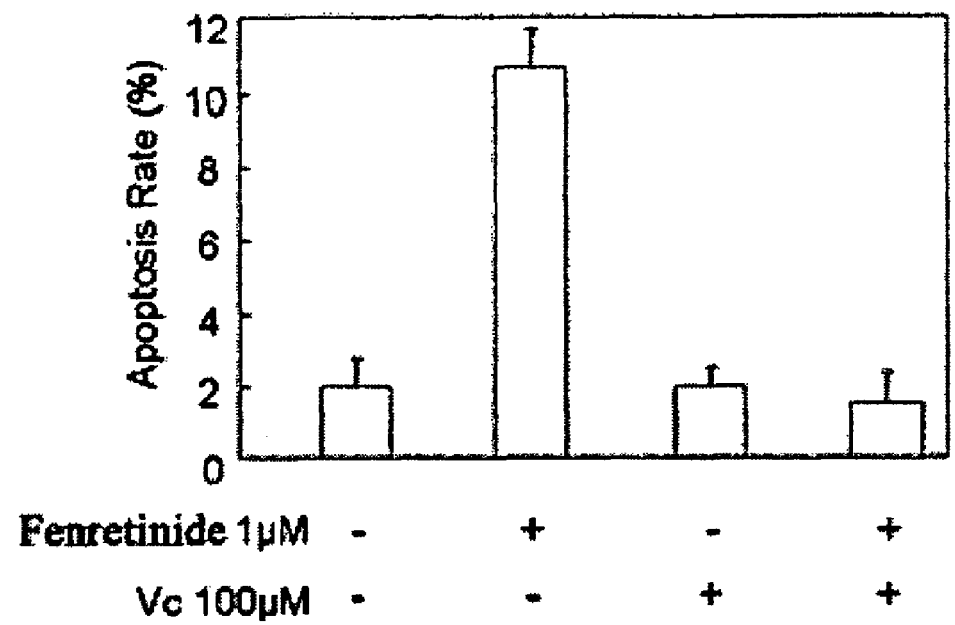
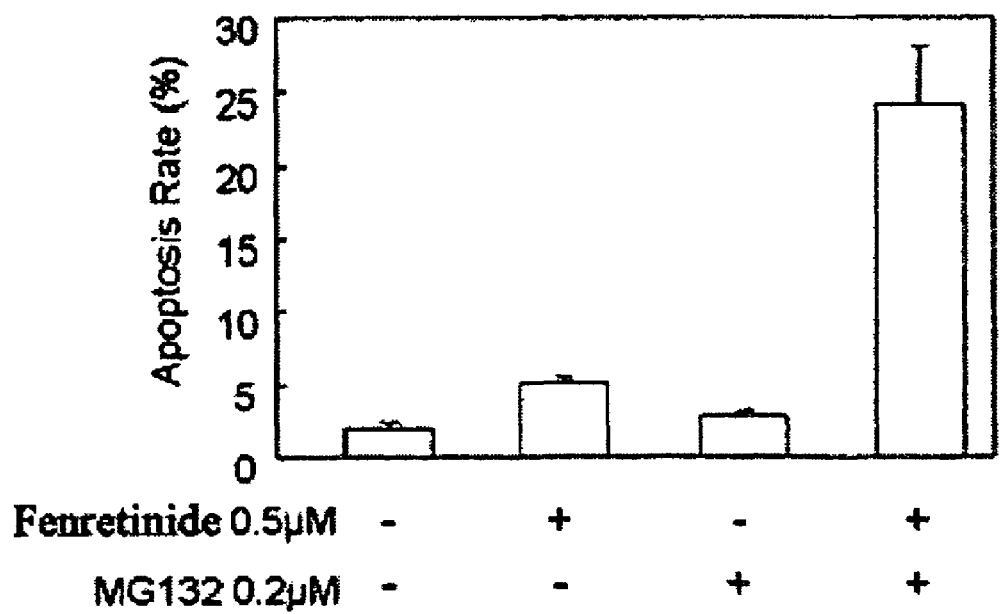
FIG. 10

TABLE 1

| No. | Age/Sex | Phase | WBC(×109/L) | Mutation | BCR-ABL variant |
|---|---|---|---|---|---|
| 1 | 25/F | CP | 90 | ND | b3a2 |
| 2 | 42/F | BP | 202 | - | b3a2 |
| 3 | 37/M | CP | 201 | - | b3a2 |
| 4 | 26/M | CP | 216 | - | b3a2 |
| 5 | 34/F | CP |  | ND | ND |
| 6 | 40/M | CP | 195 | - | ND |
| 7 | 65/M | CP | 45 | - | b3a2 |
| 8 | 26/M | CP | 300 | - | b3a2 |
| 9 | 19/M | CP | 403 | - | b2a2 |
| 10* | 52/F | CP | 40 | Y253H | ND |
| 11* | 33/M | CP | 10 | - | ND |
| 12* | 44/M | CP | 5 | F359I | b3a2 |
| 13* | 39/F | AP | 78 | Y253H | b3a2 |
| 14 | 71/M | CP | 60 | - | b3a2 |
| 15 |  | CP |  | ND | b2a2 |
| 16 | 55/M | CP | 177 | ND | ND |
| 17 | 55/M | CP | 207 | - | b2a2 |
| 18 | 23/F | CP | 61 | - | b3a2 |
| 19 | /M | CP | 71 | - | b2a2 |
| 20 | 32/F | CP | 110 | - | b3a2 |
| 21 | 30/F | CP | 350 | - | b3a2 |
| 22 | 42/M | CP | 61 | - | b3a2 |
| 23 | 47/M | CP | 154 | - | b2a2 |
| 24 | 55/M | CP | 311 | - | b2a2 |
| 25 | 68/F | CP | 217 | ND | b3a2 |
| 26 | 21/M | CP | 27 | - | b3a2 |
| 27 | 44/M | CP | 126 | - | b2a2 |
| 28 |  | CP | 120 | ND | b3a2 |
| 29 |  | CP |  | ND | b2a2 |
| 30 | 43/F | CP | 107 | - | b2a2 |
| 31* | 30/F | CP | 6 | - | b3a2 |
| 32* | 34/M | CP | 2 | - | b3a2 |
| 33 | 36/M | CP | 219 | - | b2a2 |
| 34* | 20/M | CP | 2 | E355G | b2a2 |
| 35 | 43/M | CP |  | ND | ND |
| 36 | 55/M | CP |  | ND | ND |
| 37 | 39/M | CP |  | ND | ND |
| 38 | 41/F | CP |  | ND | ND |

FIG.20

TABLE 2

| specimens | FAB | cytogenetics | | 2.5μM 4-HPR* | | 5μM 4-HPR* | | 7.5μM 4-HPR* | |
|---|---|---|---|---|---|---|---|---|---|
| | | | | % viable | SD | % viable | SD | % viable | SD |
| AML specimens | | | | | | | | | |
| AML1 | M4 | 46,xx | | 98.3 | 1.4 | 69.3 | 1.3 | 1.77 | 0.5 |
| AML2 | ND | 46,xx,t(7,12) | | 92.4 | 4.0 | 35.7 | 0.0 | 6.6 | 0.4 |
| AML3 | M6 | ND | | 44.9 | 12.2 | 25.0 | 5.7 | 7.1 | 3.1 |
| AML4 | M1 | ND | | 66.3 | 5.7 | 8.7 | 0.5 | 0.4 | 0.2 |
| AML5 | M5 | 45,x,-x,t(8,21),9q- | | 85.2 | 2.1 | 63.6 | 9.0 | 7.7 | 0.8 |
| AML6 | M4 | 46,xy | | 97.8 | 0.2 | 86.7 | 0.4 | 29 | 2.3 |
| AML7 | M6 | 46,xy,5q- | | 1.4 | 1.0 | 1.8 | 0.3 | 1.8 | 2.3 |
| AML8 | M4 | 46,xy | | 97.7 | 0.4 | 89.7 | 1.0 | 77.3 | 7.4 |
| AML9 | MDS-RA | 43-46,xx,-5,6q-,-7,-13 | | 87.7 | 0.1 | 52.8 | 4.9 | 7.2 | 1.1 |
| AML10 | M6 | 46,xx | | 93.5 | 0.8 | 26.7 | 3.0 | 13.8 | 4.0 |
| AML11 | M4 | 46,xx | | 91.8 | 0.4 | 62.2 | 0.2 | 7.3 | 0.4 |
| AML12 | M5 | ND | | 110.1 | 0.1 | 63.9 | 0.9 | 13.6 | 2.2 |
| AML13 | ND | ND | | 96.0 | 0.4 | 63.3 | 4.9 | 10.8 | 0.7 |
| AML14 | MDS | 47,xy,+11 | | 96.5 | 0.4 | 86.7 | 1.3 | 36.4 | 1.8 |
| AML15 | M4 | 46,xy | | 98.4 | 0.1 | 88.1 | 0.8 | 17.5 | 0.2 |
| AML16 | M4 | 46,xy | | 72.8 | 1.1 | 21.5 | 0.8 | 1.2 | 0.2 |
| AML17 | M5 | 46,xy | | 75.3 | 1.5 | 19.6 | 3.1 | 0.9 | 0.1 |
| AML18 | M4 | ND | | 48.9 | 4.1 | 14.3 | 0.7 | 0.3 | 0.0 |
| AML19 | M4 | ND | | 83.3 | 1.8 | 19.0 | 0.8 | 3.8 | 0.3 |
| AML20 | ND | ND | | 62.8 | 10.9 | 0.5 | 0.2 | 0.1 | 0.0 |
| AML21 | ND | 46,xy,t(8,21) | | 77.5 | 1.2 | 24.2 | 0.2 | 1.1 | 0.4 |
| AML22 | M4 | ND | | 93.5 | 1.5 | 72.3 | 2.1 | 5.5 | 1.8 |
| AML23 | M4 | 46,xy | | 95.2 | 1.4 | 47.9 | 1.3 | 6.8 | 0.0 |
| AML24 | ND | 46,xx | | 92.2 | 0.2 | 81.3 | 0.5 | 46.5 | 1.7 |
| AML25 | ND | ND | | 77.6 | 1.7 | 9.2 | 0.0 | 0.1 | 0.0 |
| ALL specimens | | | | | | | | | |
| ALL1 | ALL-L2 | 46,xy | T | 78.2 | 1.9 | 28.3 | 0.2 | 16.1 | 0.1 |
| ALL2 | ALL-L2 | 46,xx | ND | 99.9 | 0.9 | 100.6 | 0.0 | 74.6 | 3.7 |
| ALL3 | ALL | 46,xx | ND | 102.3 | 0.4 | 54.0 | 1.0 | 6.1 | 0.3 |
| ALL4 | ALL-L2 | ND | B | 95.5 | 1.4 | 87.3 | 1.5 | 40.7 | 3.2 |
| ALL5 | ALL | ND | ND | 94.1 | 2.0 | 22.2 | 2.6 | 1.2 | 0.2 |
| ALL6 | ALL-L2 | 46,xy | B | 41.5 | 9.1 | 0.5 | 0.0 | 1.1 | 1.6 |
| ALL7 | ALL | 52-56,xy | Mix | 83.7 | 0.7 | 32.0 | 2.2 | 4.3 | 1.4 |
| ALL8 | ALL-L2 | ND | | 98.1 | 2.2 | 68.1 | 0.0 | 3.0 | 0.3 |
| ALL9 | ALL-L2 | ND | | 98.8 | 1.5 | 100.0 | 1.2 | 71.6 | 1.3 |
| ALL10 | ALL-L2 | ND | B | 83.2 | 2.4 | 67.4 | 0.6 | 25.5 | 3.6 |
| ALL11 | ALL-L2 | 46,xy,t(3:9) | B | 94.0 | 0.5 | 87.6 | 2.2 | 11.7 | 0.3 |
| ALL12 | ALL-L2 | 46,xx | | 91.4 | 0.2 | 76.0 | 1.4 | 42.2 | 4.4 |
| ALL13 | ALL-L2 | ND | B | 87.6 | 1.2 | 48.9 | 0.1 | 3.3 | 0.3 |
| ALL14 | ALL-L2 | 46,xy | T | 44.7 | 1.2 | 2.1 | 0.1 | 0.4 | 0.3 |
| ALL15 | ALL-L2 | 46,xy | | 99.3 | 0.1 | 63.4 | 1.9 | 3.1 | 0.2 |
| ALL16 | ALL-CML | 47,xx,ph1 | B | 88.7 | 0.4 | 60.0 | 3.1 | 7.0 | 0.7 |
| ALL17 | ALL-CML | ND | | 97.6 | 0.8 | 88.4 | 1.3 | 42.6 | 1.0 |
| Normal specimens | | | | | | | | | |
| N1 | | | | 115.8 | 1.8 | 118.1 | *1.1 | 91.9 | 2.5 |
| N2 | | | | 95.0 | 8.8 | 95.2 | 0.0 | 74.6 | 8.8 |
| N3 | | | | 90.2 | 0.9 | 85.5 | 1.1 | 23.3 | 2.0 |
| N4 | | | | 81.2 | 7.0 | 87.2 | 0.5 | 78.2 | 3.1 |
| N5 | | | | 102.9 | 2.3 | 94.3 | 0.9 | 17.6 | 0.8 |
| N6 | | | | 98.9 | 0.4 | 97.9 | 0.0 | 28.1 | 0.7 |
| N7 | | | | 99.3 | 0.7 | 99.2 | 0.0 | 82.8 | 1.3 |
| N8 | | | | 101.1 | 0.7 | 99.3 | 0.5 | 68.4 | 1.7 |

Note: *4-HPR=fenretinide

FIG.21

TABLE 3

| Time | Sample | 4-oxo-4-fenretinide (μM) | | | |
|---|---|---|---|---|---|
| | | 1.25 | 2.5 | 5 | 10 |
| 24h | Quiescent HL60 | 0.97 | 0.94 | 0.72 | 0.51 |
| | Proliferating HL60 | 1.09 | 1.13 | 1.11 | 1 |
| 48h | Quiescent HL60 | 0.82 | 0.77 | 0.46 | 0.48 |
| | Proliferating HL60 | 1.08 | 1.09 | 1.08 | 0.84 |

FIG.22

USE OF FENRETINIDE OR BIOACTIVE DERIVATIVES THEREOF AND PHARMACEUTICAL COMPOSITIONS COMPRISING THE SAME

TECHNICAL FIELD

The present invention relates to a new use of fenretinide or bioactive derivatives thereof, in particular to the use of fenretinide or bioactive derivatives thereof in the preparation of a medicament for eliminating or killing tumor stem cells (TSCs) or particularly hematologic tumor stem cells or for treating and/or preventing a tumor disease or hematologic tumor disease originating from tumor stem cells or hematologic tumor stem cells in a subject. The invention further relates to a new use of fenretinide or bioactive derivatives thereof in combination with at least one additional anti-tumor agent, a pharmaceutical composition comprising said fenretinide or bioactive derivatives thereof and at least one additional anti-tumor agent, a method of screening said other anti-tumor agent, a method of eliminating or killing tumor stem cells or particularly hematologic tumor stem cells in a subject with said fenretinide or bioactive derivatives thereof, as well as a method of eliminating or killing tumor stem cells and particularly hematologic tumor stem cell, and tumor cells derived from tumor stem cells or particularly from hematologic tumor stem cells in a subject with said fenretinide or bioactive derivatives thereof in combination with other anti-tumor agent(s).

BACKGROUND ART

In the past decades, accumulating knowledge in stem cell biology has exerted extensive impacts on the understanding of human ontogenesis and homeostasis, and particularly of the genesis of human malignancy and the related therapies (see e.g., Bonnet and Dick, 1997). Stem cells have been shown to be present in a variety of mammalian tissue systems, including skin, gut, central nervous system, and hematopoietic systems (see e.g., Blanpain et al., 2004). Stem cells are centrally defined by the capabilities of self-renewal, differentiation into a broad spectrum of specific lineages and long-term proliferation. In view of the analogies between normal stem cells and tumorigenic cells in terms of their physiological features, tumorigenic cells have been recognized as tumor stem cells, and there are indeed increasing documentations confirming the existence of tumor stem cells in hematologic cancers, central nervous system tumors and breast tumors (see e.g., Bonnet and Dick, 1997; Cobaleda et al., 2000; Jordan et al., 2006).

Tumor stem cells distinguish themselves from normal stem cells and classically-defined tumor cells. As compared with the normal counterparts, tumor stem cells display certain unique physiological characteristics. For example, leukemia stem cells exhibit abnormal activation of nuclear factor kappa B and elevated expression level of CD123, interferon regulatory factor 1 (IRF-1) and death-associated protein (DAP) kinase. Unlike the classically-defined tumor cell populations, tumor stem cells act as parent cells thereof and are endowed with limitless self-renewal capacities and the multiple lineages-differentiating potentials.

In the field of tumor-related study and therapy, emerging experimental and clinical data have shown that many tumors arise from a rare population of cells, namely tumor stem cells (see e.g., Jordan et al., 2006). Tumor stem cells are oncogenic, poorly differentiated and capable of leading to self-renewal of tumor cell populations (see e.g., Hope et al., 2004). First demonstrated was the existence of leukemia stem cells (LSCs) (see e.g., Lapidot et al., 1994). Analogous to normal hematopoietic stem cells (HSCs), LSCs comprise only a small fraction of leukemia cells, belong to the top of hierarchical organization with poorly differentiated status and display limitless self-renewal capacity. They account for the genesis of leukemia progenitor cells with limited proliferation capacity and downstream leukemia cells at different differentiation degrees, and consequently lead to the onset of leukemia. Therefore, in targeted therapies for tumors, tumor stem cells represent a promising target for drug design and screening.

Most conventional anti-tumor agents act on those mature differentiated tumor cells downstream the tumor stem cells, and are extremely insensitive to those poorly differentiated tumor stem cells having limitless proliferation potentials. Thus, most tumor patients, although can be clinically alleviated, frequently suffer from drug resistance and tumor relapse due to the lack of effective drugs specifically targeting tumor stem cells. For example, chronic myelogenous leukemia (CML) is a CML stem cell-originated disorder (see e.g., Huntly and Gilliland, 2004), characterized mainly by the oncogenic BCR-ABL fusion protein resulting from gene translocation, thereby exhibiting abnormal tyrosine kinase activity. A well-designed inhibitor targeted to this tyrosine kinase, imatinib (STI571, Gleevec), can effectively kill leukemia cells (see e.g., Deininger et al., 2000). However, many CML patients often suffer from drug resistance and relapse following long-term of imatinib administration. Molecular diagnosis shows that BCR-ABL positive cells remain in almost all the patients, suggesting that tyrosine kinase targeted inhibitor imatinib alone cannot eliminate all of the leukemia cells, especially leukemia stem cells (see e.g., Graham et al., 2002). Another example is acute myelogenous leukemia (AML), characterized by premature arrest of myeloid development and the subsequent accumulation of large numbers of non-functional leukemic blasts, including AML stem cell population (see e.g., Bonnet and Dick, 1997). Since the persistence of surviving AML stem cell population after the conventional chemotherapy, like cytosine arabinoside (Ara-C) that mainly kill dividing cells through interfering with DNA replication (see e.g., Guan and Hogge, 2000), it is always hard to achieve durable and complete remission (see e.g., Guzman et al., 2002; Guan et al., 2003).

Thus, there apparently is an urgent need for therapeutic strategies, specifically ablating tumor stem cells while sparing normal stem cells, which will not only overcome the drug resistance of tumor and the tumor relapse, but also bring great benefits for prevention and permanent cure of tumor disease originating from tumor stem cells.

Surprisingly, the inventors have found that, fenretinide or bioactive derivatives thereof can specifically induce the apoptosis of primitive tumor cells, particularly quiescent $CD34^+$ $CD38^-$ leukemia stem cells, and can also kill $CD34^+CD38^+$ leukemia progenitor cells having similar physiological features to leukemia stem cells, while having no significant effect on normal hematologic stem cells. The inventors have further found that combination therapy associated with fenretinide or bioactive derivatives thereof can achieve better therapeutic effect. Moreover, the inventors have established a method for effectively screening anti-tumor agents that can combine with fenretinide or bioactive derivatives thereof to induce apoptosis of tumor cell, especially hematologic tumor cells.

DESCRIPTION OF INVENTION

Summary of Invention

In the first aspect, the present invention provides a new medical use of fenretinide or bioactive derivatives thereof.

According to the first aspect, the present invention provides in the second aspect that new medical use of said fenretinide or bioactive derivatives thereof in combination with other anti-tumor agents.

According to the second aspect, the present invention provides in the third aspect a pharmaceutical composition for said new medical use comprising said fenretinide or bioactive derivatives thereof and at least one additional anti-tumor agent.

In the fourth aspect, the present invention provides a method of screening the additional anti-tumor agent for combining with fenretinide or bioactive derivatives thereof for use in the new medical use.

In the fifth aspect, the present invention provides a method of eliminating or killing tumor stem cells and tumor cells derived from tumor stem cells, particularly hematologic tumor stem cells and hematologic tumor cells derived from hematologic tumor stem cells.

DETAILED DESCRIPTION OF INVENTION

The inventors have found that, fenretinide or bioactive derivatives thereof, particularly fenretinide, can specifically induce the apoptosis of tumor stem cells while having no significant effect on normal stem cells. For hematologic tumors, for example, fenretinide has been found as capable of inducing apoptosis of $CD34^+CD38^-$ cell subpopulations derived from a patient sample suffering from hematologic cancer while sparing normal hematologic stem cells, and meanwhile capable of killing $CD34^+CD38^+$ leukemia progenitor cells.

The inventors have also found that, fenretinide or bioactive derivatives thereof, particularly fenretinide, functions mainly by altering the redox balance in hematologic tumor stem cells and/or progenitor cells, elevating the active oxygen level in those primitive and mostly quiescent cells to an extent exceeding the endurable antioxidant threshold thereof, thereby specifically inducing apoptosis.

The inventors have further found that, the process of apoptosis induced by fenretinide or bioactive derivatives thereof, particularly fenretinide, in hematologic tumor stem cells and/or progenitor cells can be characterized by molecular events such as oxidative stress, endoplasmic reticulum stress, unfolded protein response and proteasome activation. Of note, the process of apoptosis is related to the activation of stress-responsive transcription factors HSF1 and NRF2, and the expression of their target genes, which thus mediates the transmission of upstream active oxygen signaling generated by the drug to downstream cellular stress responses.

Based on the above findings, the present invention provides in the first aspect use of fenretinide or bioactive derivatives thereof in the preparation of a medicament for eliminating or killing tumor stem cells or for treating and/or preventing a tumor disease originating from tumor stem cells in a subject. Further, the first aspect of the invention provides use of fenretinide in the preparation of a medicament for treating and/or preventing a tumor disease in which eliminating or killing tumor stem cells is beneficial in inhibiting the development of drug resistance in tumor and the relapse of the disease.

Fenretinide according to the present invention is a synthetic all-trans-retinoid acid derivative with the chemical name of N-(4-hydroxyphenyl)retinamide (CAS Registry number 65646-68-6), which can be synthesized by the method as described in U.S. Pat. No. 4,190,594.

Bioactive derivatives of fenretinide according to the present invention refer to those derivatives formed by chemical modification or biological metabolism of fenretinide and remaining or even having enhanced biological activities of fenretinide, including but not limited to active metabolite of fenretinide such as 4-oxo-fenretinide, possible solvates, possible prodrugs and possible pharmaceutically acceptable salts thereof. It should be appreciated that, said solvates, prodrugs and pharmaceutically acceptable salts has the conventional meaning in the present art well known to those skilled persons. The details can be seen in Remington: The Science and Practice of Pharmacy ($21^{st}$ Ed., ISBN: 9780781746731, Jun. 15, 2005).

According to the present invention, fenretinide or pharmaceutically acceptable salts thereof is preferably used.

The term "subject" used herein is well known to a person skilled in the art, and in the present invention, it refers particularly to mammals, more particularly to human subjects suffering from the disease described herein, e.g. hematologic tumor, and thereby in need of the treatment or prevention by the pharmaceutical composition or method of the present invention.

The term "tumor" according to the present invention includes hematologic tumors and solid tumors. Correspondingly, the tumor stem cells according to the present invention include hematologic tumor stem cells and solid tumor stem cells. Further, the hematologic tumor stem cells mainly refer to $CD34^+CD38^-$ cell subpopulation derived from a specimen of hematologic tumor patient, said cells express CD34 but do not express CD38. The solid tumor stem cells according to the present invention refer to a small fraction of solid tumor cells displaying extensive proliferating and tumorigenic capacity. The hematologic tumor progenitor cells according to the present invention refer to $CD34^+CD38^+$ cell subpopulation derived from a hematologic tumor patient, said cells express both CD34 and CD38.

The term "hematologic tumor" according to the present invention includes but not limited to leukemia and malignant lymphoproliferative disorder. Further, said leukemia includes but not limited to chronic myelogenous leukemia (CML), acute myelogenous leukemia (AML), myelodysplastic syndrome, acute lymphoid leukemia (ALL), chronic lymphoid leukemia (CLL). Further, said malignant lymphoproliferative disorder includes but not limited to lymphoma and multiple myeloma (MM); and said lymphoma includes but not limited to non-Hodgkin's lymphoma, Burkitt's lymphoma, and small cell and/or large cell follicular lymphoma.

The term "solid tumor" according to the present invention especially refers to breast cancer, cancer of the colon and generally the GI tract cancer including gastric cancer, hepatoma; lung cancer, in particular small-cell lung cancer and non-small-cell lung cancer, renal cancer, mesothelioma, glioma, squamous cell carcinoma of the skin, head and neck cancer, genitourinary cancer, e.g. cervical, uterine, ovarian, testicles, prostate or bladder cancer; Hodgkin's disease, carcinoid syndrome or Kaposi's sarcoma. In a preferred embodiment of the invention, the solid tumor to be treated is selected from gastric cancer, neuroblastoma, breast cancer, colorectal cancer, ovarian cancer, renal cancer, lung cancer, especially gastric cancer, and ovarian cancer.

In a preferred embodiment of the invention, said tumor is hematologic tumor, preferably leukemia. Therefore, the first aspect of the invention preferably provides the use of fenretinide or bioactive derivatives thereof in the preparation of a medicament for eliminating or killing hematologic tumor stem cells or for treating and/or preventing a hematologic tumor disease originating from hematologic tumor stem cells in a subject. Further, the first aspect of the invention provides the use of fenretinide or bioactive derivatives thereof in the preparation of a medicament for treating and/or preventing a hematologic tumor disease in which eliminating or killing hematologic tumor stem cells is beneficial in inhibiting the development of drug resistance in the tumor and the relapse of the disease.

According to the present invention, the expressions of "a tumor disease originating from tumor stem cells", "a tumor disease in which eliminating or killing tumor stem cells is beneficial in inhibiting development of drug resistance and relapse of the disease", "a hematologic tumor disease originating from hematologic tumor stem cells" and "a hematologic tumor disease in which eliminating or killing tumor hematologic tumor stem cells is beneficial in inhibiting development of drug resistance and relapse of the disease", respectively refer to "a tumor disease, in terms of genesis and development of human malignancy, originating from populations of tumor stem cells with limitless self-renewal and the multiple lineages-differentiating capacities", "a tumor disease which will be effectively and completely cured by eliminating or killing tumor stem cells, with the contrast to the occurrence of drug resistance and tumor relapse by eliminating or killing tumor cells", "a hematologic tumor disease, in terms of genesis and development of human malignancy, originating from populations of hematologic tumor stem cells with limitless self-renewal and the multiple lineages-differentiating capacities", "a hematologic tumor disease which will be effectively and completely cured by eliminating or killing hematologic tumor stem cells, with the contrast to the occurrence of drug resistance and tumor relapse by eliminating or killing hematologic tumor cells".

The inventors have further found that, the combination therapy associated with fenretinide can achieve better therapeutic effect. The test applying the combination according to the present invention to hematologic tumor shows that fenretinide in combination with at least one additional anti-tumor agent can synergistically inhibit proliferation and induce apoptosis of hematologic tumor cells, while having no significant toxic and side effect on normal control hematologic stem cells, wherein fenretinide mainly acts on the hematologic tumor stem cells and progenitor cells subpopulation, while another combined agent mainly acts on relatively mature hematologic tumor cell subpopulation. For example, it has been demonstrated herein that the combinations of fenretinide with BCR-ABL tyrosine kinase-targeted inhibitors, fenretinide with conventional chemotherapeutics, fenretinide with proteasome inhibitors, fenretinide with Ara-C and MG132, and fenretinide with imatinib and MG132 show synergistic induction of apoptosis in hematologic tumor cells. The test of applying the combination according to the present invention to solid tumors also shows that fenretinide in combination with at least one additional anti-tumor agent can synergistically inhibit proliferation and induce apoptosis of tumor cells, for example, the synergistic effect of fenretinide combined with tetrandrine on apoptosis in gastric tumor cells.

The term "synergistic" or "synergistically" according to the present invention means that the effect produced by the combination is greater than the sum of the effects produced by each agent alone. For the present invention, the synergistic therapeutic effect is achieved under the action of the combined administration in hematologic tumor, wherein it is to be emphasized that fenretinide are primarily effective on subpopulations of hematologic tumor stem cells and/or progenitor cells, and can also enhance the capacity of another conventional anti-tumor agent in killing more mature cell subpopulations in hematologic tumor.

Based on the above findings, the present invention provides in the second aspect a new medical use of fenretinide or bioactive derivatives thereof in combination with at least one additional anti-tumor agent. Further, the second aspect of the invention provides use of fenretinide or bioactive derivatives thereof in combination with at least one additional anti-tumor agent in the preparation of a medicament for simultaneous, sequential and/or separate administration for synergistically inducing apoptosis of tumor cells in a subject to treat and/or prevent a tumor disease in a subject.

Also based on the above findings, the present invention provides in the third aspect pharmaceutical composition comprising a therapeutically effective amount of fenretinide or bioactive derivatives thereof, a therapeutically effective amount of at least one additional anti-tumor agent, and optionally pharmaceutically acceptable carrier, wherein said at least one additional anti-tumor agent is to be administered simultaneously, sequentially or separately with fenretinide or bioactive derivatives thereof to synergistically induce apoptosis of tumor cells in the subject.

The term "additional anti-tumor agent" used herein refers to an anti-tumor drug distinct from fenretinide or bioactive derivatives thereof. Said at least one additional anti-tumor agent includes but not limited to cell cycle-specific chemotherapeutic agents, BCR-ABL tyrosine kinase-targeted inhibitors, proteasome inhibitors and conventional chemotherapeutic agents having different action mechanism with the former.

Said cell cycle-specific chemotherapeutic agents refer to those chemotherapeutics eliminating or killing proliferating cells at the specific phase of cell cycle, including but not limited to, arabinoside, 5-fluorouracil, hydroxyurea, 6-mercaptopurine, 6-thioguanine, fludarabine, methotrexate. For the present invention, cell cycle-specific chemotherapeutic agent in the second and third aspect is preferably arabinoside, the mechanism of which is through interfering with DNA replication to eliminate or kill proliferating cells, and which can be purchased from Sigma.

Said BCR-ABL tyrosine kinase above exhibits abnormal tyrosine kinase activity and results from the oncogenic BCR-ABL fusion gene created during the form of Philadelphia chromosome due to chromosome translocation. BCR-ABL tyrosine kinase targeted inhibitor can inhibit this abnormal tyrosine kinase activity, and thus lead to the apoptosis of BCR-ABL positive cells, including but not limited to imatinib, dasatinib and nilotinib. In some preferable embodiments of the present invention, imatinib in combination with fenretinide or bioactive derivatives thereof is utilized in a new medical use of the present invention; imatinib, fenretinide or bioactive derivatives thereof and optionally pharmaceutically acceptable carrier are comprised in the pharmaceutical composition of the present invention. The chemical name of imatinib is 4-[(4-methylpiperazin-1-yl)methyl]-N-[4-methyl-3-[(4-(3-pyridinyl)-pyrimidin-2-yl)amino]phenyl]benzamide, which can be purchased from Novatis in Switzerland.

Said proteasome inhibitors above refer to those anti-tumor drugs acting through the blockage of the ubiquitin-proteasome pathway, including but not limited to bortezomib, BzLLLCOCHO and MG-132. BzLLLCOCHO is represented by the formula of Bz-Leu-Leu-Leu-COCHO, which can be produced as described in the literature (e.g., Lynas et al. 1998). The chemical structure of MG-132 is N-[(phenylmethoxy)-carbonyl]-L-leucyl-N-[(1S)-1-formyl-3-methylbutyl]-L-Leucinamide, available from Sigma. For the present invention, proteasome inhibitor in the second and third aspect is preferably bortezomib, with the chemical name of [(1R)-3-methyl-1-[[(2S)-1-oxo-3-phenyl-2-[(pyrazinylcarbonyl)amino]propyl]amino]butyl]boronic acid, which can be purchased from Millennium Pharmaceuticals in USA.

Said conventional chemotherapeutic agents having different action mechanism with the former above refer to a series of conventional chemotherapeutics for eliminating or killing proliferating cells at the various phases of cell cycle, including but not limited to idarubicin, vincristine, doxorubicin, daunorubicin, mitoxantrone, vinblastine, vindesin, harringtonine, etoposide, teniposide, L-asparaginase, cyclophosphamide, cisplatin, and preferably idarubicin.

The term "combination" used herein means that said fenretinide or a bioactive derivative thereof and at least one additional anti-tumor agent can be used as a single unit dosage form, as separate unit dosage forms or within a single therapeutic regimen. Correspondingly, the term "simultaneously, sequentially or separately" used herein means that said fenretinide or a bioactive derivative thereof and at least one additional anti-tumor agent can be administered simultaneously as a single unit dosage form or as separate unit dosage forms, or can be administered separately at different time in any order of administration as separate dosage forms or within a single regimen.

The pharmaceutical composition of the invention can be prepared in a manner known, per se, e.g., by means of conventional mixing, granulating, coating, dissolving or lyophilizing processes, into a dosage form suitable for oral administration, parenteral administration or local administration, selected from: tablet, capsule, granule, injection, powder for injection, transdermal patch, ointment, gel, suppository, oral solution, oral suspension, emulsion for injection, oral emulsion, sustained release tablet, controlled release tablet, etc. Although in principle any dosage form can be used clinically, the pharmaceutical composition of the invention comprising fenretinide or a bioactive derivative thereof and another anti-tumor agent is preferably administered orally.

The pharmaceutical composition preferably administered through oral route in the present application can be prepared by, for example, combining the active ingredient(s) with one or more solid carrier, if necessary, granulating the resulting mixture, and processing the resulting mixture or granulate, if desirable or necessary, after the addition of a suitable adjuvant, into tablets or kernels.

Further pharmaceutical compositions preferably administered orally in the present application include hard capsules consisting of gelatin and also soft, sealed capsules consisting of gelatine and a plasticiser, such as glycerine or sorbitol. In soft capsules, the active ingredient is preferably dissolved or suspended in suitable liquid vehicles, it being possible to add also stabilizers and/or detergents.

The pharmaceutical composition of the invention, in addition to fenretinide or a bioactive derivative thereof as the main active ingredient, further comprises a pharmaceutically acceptable carrier and at least one additional anti-tumor agent as co-agent. The term "pharmaceutically acceptable carrier" includes pharmaceutically acceptable carriers or excipients well known in the pharmaceutical field, such as liquid or solid fillers, diluents, excipients, solvents or encapsulating materials. Said carriers and excipients shall be "acceptable" for their compatibility with other components and nontoxicity in patients. The examples useful as pharmaceutically acceptable carriers include: saccharides, such as lactose, glucose and sucrose; starches, such as corn starch and potato starch; celluloses and derivatives thereof, such as sodium carboxymethylcellulose, ethyl cellulose and cellulose acetate; gum tragacanth powder; malt; gelatin; talcum powder; excipients, such as cocoa butter and suppository wax; oils, such as peanut oil, cottonseed oil, safflower oil, sesame oil, olive oil, corn oil and soy oil; ethylene glycols, such as propanediol; polyols, such as glycerol, sorbitol, mannitol and polyethylene glycol; esters, such as ethyl oleate and ethyl laurate; agar; buffers, such as magnesium hydroxide and aluminum hydroxide; alginic acid; pyrogen-free water; isosmotic saline; Ringer's solution; ethanol; phosphate buffer solution; and other innoxious compatible substances for the pharmaceutical preparation.

The pharmaceutical composition of the invention can further comprise adjuvants such as preservatives, solubilizers, stabilizers, wetting agents, emulsifiers, sweeteners, colorants, flavors, osmosis-regulating salts, buffers, masking agents or antioxidants. In addition, by introducing absorption-delaying components into the pharmaceutical dosage form, the absorption thereof can be prolonged.

It should be understood by a person skilled in the art that although the pharmaceutical composition mentioned hereinabove further comprises a pharmaceutically acceptable carrier, when fenretinide or a bioactive derivative thereof and at least one additional anti-tumor agent are used as a medicament for humans or animals, they can also be administered as such, i.e. the present invention can also be carried out without adding said pharmaceutically accepted carriers. For the use of the pharmaceutical combination as well as the pharmaceutical composition according to the present invention, the dose level and administration period of the pharmaceutically active agents can be varied, and surely shall be adapted to the individual requirement in each specific case. An exemplary dosage range for fenretinide or a bioactive derivative thereof is 50 or 100 mg to 500 mg or 1000 mg, 2000 or 3000 mg/m$^2$ body weight per day, preferably 100 mg/m$^2$, 200 mg/m$^2$ or 400 mg/m$^2$ body weight per day; for other anti-tumor agents such as BCR-ABL tyrosine kinase inhibitor imatinib, the dosage range is 200 mg, 400 mg, 600 mg, 800 mg once per day, or 400 mg twice per day, preferably 200 mg, 400 mg, 600 mg once per day; for example, the dosage range for the chemotherapeutic agent arabinoside is 0.5 mg/kg, 1.0 mg/kg, 1.5 mg/kg or 2 mg/kg body weight per day, preferably 1 mg/kg body weight per day, by intravenous injection; for example, the dosage range for the proteasome inhibitor bortezomib is 0.7 mg/m$^2$, 1.0 mg/m$^2$, 1.3 mg/m$^2$ for each single injection, twice a week, preferably 1.0 mg/m$^2$ for each single injection, twice a week.

For the combination using fenretinide of the invention or a bioactive derivative thereof and at least one additional anti-tumor agent and the pharmaceutical composition comprising the same, the administration and dose regimens can be determined depending on factors, including type, species, age, weight, sex of the subject and the type of tumor/cancer to be treated; severity (i.e. stage) of the tumor/cancer to be treated; administration route; functions of kidney and liver of the patient; and the specific compound or salt thereof to be used. One can use an administration/dose regimen to, for example, prevent, inhibit (wholly or partially) the disease or stop the progression of the disease.

Based on the findings above, the fourth aspect of the present application provides a method for in vitro screening anti-tumor agent, which is to be combined with fenretinide or bioactive derivatives thereof to synergistically induce apoptosis of tumor cells, comprising steps of:

1) contacting tumor cells with (a) an effective amount of fenretinide or bioactive derivatives thereof and (b) candidate anti-tumor agent and determining the apoptosis of cells;

2) contacting tumor cells with (a) an effective amount of fenretinide or bioactive derivatives thereof and determining the apoptosis of cells;

3) contacting tumor cells with (b) candidate anti-tumor agent and determining the apoptosis of cells; and 4) if the apoptosis in step 1) is greater than the sum of apoptosis in step 2) and step 3), said candidate anti-tumor agent can be recognized as capable of combining with fenretinide or bioactive derivatives thereof to synergistically induce apoptosis of tumor cells.

The fifth aspect of the invention provides a method of eliminating or killing tumor stem cells in a subject, comprising the step of administering fenretinide or a bioactive derivative thereof in an amount effective in inducing apoptosis of tumor stem cells. Further, the present invention provides a method of eliminating or killing hematologic tumor stem cells in a subject, comprising the step of administering fenretinide or a bioactive derivative thereof in an amount effective in inducing apoptosis of said stem cells. In other words, either of the above methods is intended to use fenretinide or a bioactive derivative thereof alone for eliminating or killing tumor, particularly hematologic tumor stem cells.

The fifth aspect of the invention further provides a method of eliminating or killing tumor stem cells and tumor cells derived from tumor stem cells, which comprises the step of administering a therapeutically effective amount of at least one additional anti-tumor agent before, during or after the step of administering fenretinide or a bioactive derivative thereof in an amount effective in inducing apoptosis of tumor stem cells. Further, the present invention provides a method of eliminating or killing hematologic tumor stem cells and hematologic tumor cells derived from hematologic tumor stem cells in a subject, which comprises the step of administering a therapeutically effective amount of at least one additional anti-tumor agent before, during or after the step of administering fenretinide or a bioactive derivative thereof in an amount effective in inducing apoptosis of hematologic tumor stem cells. In other words, either of the above two methods is intended to use fenretinide or a bioactive derivative thereof in combination with at least one additional anti-tumor agent for eliminating or killing tumor stem cell and tumor cells derived therefrom, particularly hematologic tumor stem cells and hematologic tumor cells derived therefrom.

It shall be understood that with respect to fenretinide or bioactive derivatives thereof, tumors and stem cells thereof, hematologic tumors and stem cells and progenitor cells thereof, solid tumors as well as other anti-tumor agents, the general definitions and preferable definitions as given above are also applicable for the screening method in the fourth aspect and the therapeutic method in the fifth method of the invention.

Furthermore, the present invention includes a "kit" comprising fenretinide or a bioactive derivative thereof and at least one additional anti-tumor agent, i.e. one formed by formulating fenretinide or a bioactive derivative thereof and at least one additional anti-tumor agent separately into unit dosage forms, then combining said separate unit dosage forms. In such a case, fenretinide or a bioactive derivative thereof and at least one additional anti-tumor agent provided in separate unit forms can be easily administrated to a subject in a simultaneous, sequential or separate manner.

In the Examples of the present invention, the results show that fenretinide can more effectively induce apoptosis in quiescent leukemia cells than in proliferating cells (see Example 1), and inhibit colony forming in primitive leukemia cells (see Example 2). Meanwhile, fenretinide can specifically target quiescent $CD34^+CD38^-$ LSCs isolated from CML, AML, and ALL patient specimens, while sparing normal HSCs (see Examples 3 and 4). In a series of studies, the inventors also examined the association between the susceptibilities of leukemia cells to fenretinide and the increased levels of intracellular ROS (see Example 5), explored the molecular events involved in the fenretinide-induced apoptosis (see Example 6), and identified the pharmacological targets of fenretinide intervention (see Example 7), and summarized the dynamic changes of the events involved in fenretinide-induced apoptosis (see Example 8). In another series of studies, the inventors also provided several fenretinide-related-to combination therapies, as illustrated in co-treatment of AML with fenretinide and Ara-C (see Example 9), co-treatment of CML with fenretinide and imatinib (see Example 10), triple treatment of AML with fenretinide, Ara-C and MG132 (see Example 11) and triple treatment of CML with fenretinide, imatinib and MG132 (see Example 12), and co-treatment of gastric tumor with fenretinide and tetrandrine (see Example 13). Finally, the inventors showed the use of fenretinide's bioactive derivative for the elimination or killing of leukemia stem cells (see Examples 14 and 15), and illustrated the preparation comprising fenretinide (see Preparation Example).

Although most experiments as described in the context of the present application are related to hematological tumors from a great number of clinic specimens, a skilled artisan will understand that the benefit effects shown in these experiments can be easily embodied in clinical practice in human.

All patents, patent applications, provisional applications, and publications referred to or cited herein are incorporated by reference in their entirety, including all figures and tables, to the extent they are not inconsistent with the explicit teaching of this specification.

Following are examples which illustrate procedures for practicing the invention. These examples should not be construed as limiting.

BRIEF DESCRIPTION OF THE DRAWINGS

FIGS. 10A and 10B show the effects of blocking ROS and inhibiting proteasome activity on apoptosis induction of leukemic NB4 cells by fenretinide. (A) Abrogation of fenretinide-induced apoptosis by vitamin C. (B) Synergistic induction of cell apoptosis by proteasome inhibitor MG132 and fenretinide.

FIG. 20 gives TABLE 1, which summaries basic information of CML patients. Of the 38 patients, 31 were in the newly diagnosed chronic phase, 5 with imatinib-resistant, one in the blast crisis phrase and one with imatinib-resistant turned to the accelerated phase.

FIG. 21 gives TABLE 2, which shows the effects of fenretinide treatment on $CD34^+$ populations of acute leukemia patients and normal donors, including 25 AML, 17 ALL, and 8 normal specimens.

FIG. 22 gives TABLE 3, which shows the effects of 4-oxo-N-(4-hydroxyphenyl)retinamide(4-oxo-4-fenretinide) on cell viability of quiescent and proliferating leukemia cells.

EXAMPLES

Figure 1:
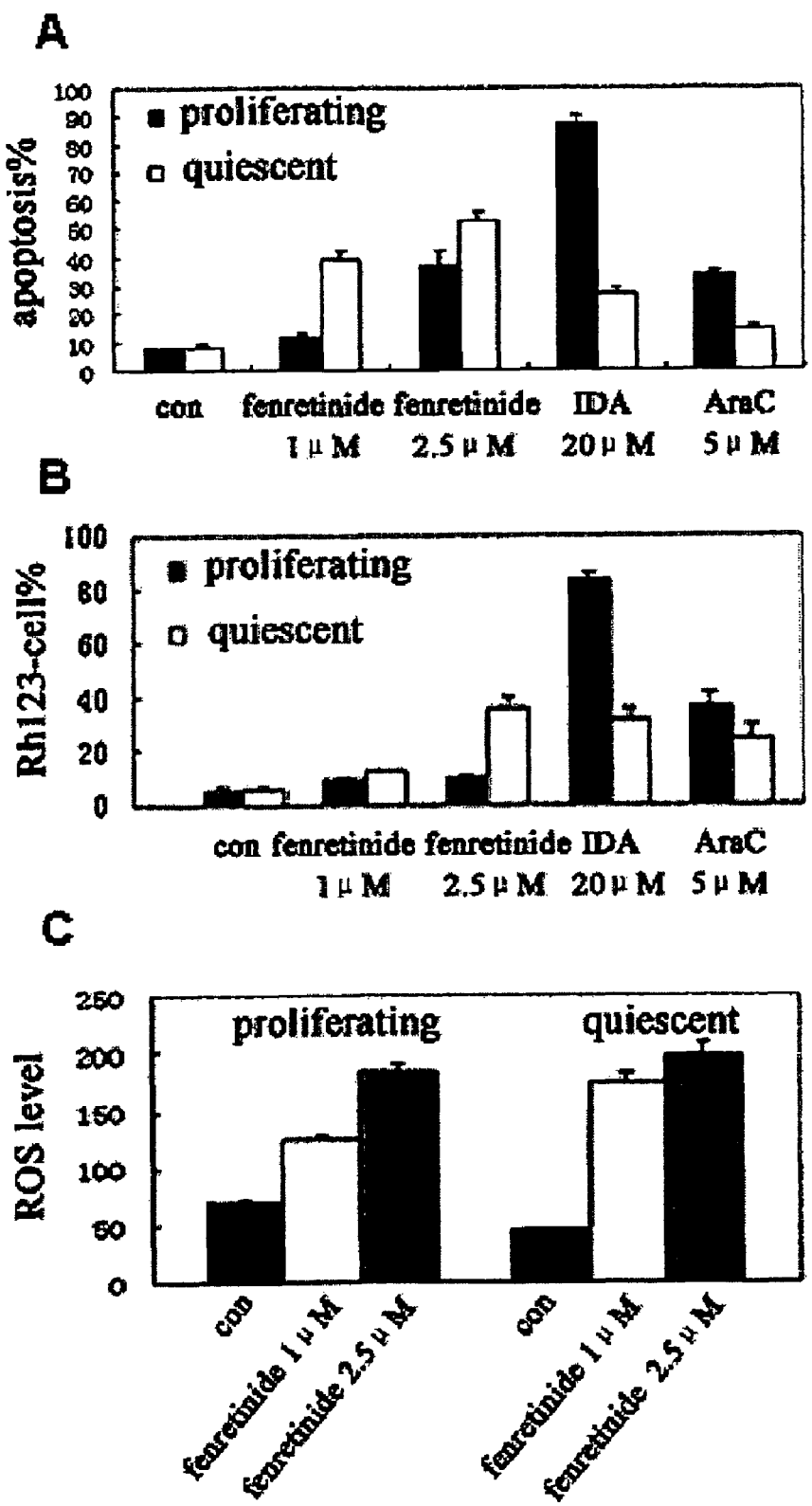
FIGS. 1A and 1B and 1C show effects of fenretinide on apoptosis, Mitochondrial transmembrane potential (MTP) and reactive oxygen species (ROS) abundance in proliferating leukemia-derived HL60 cells and serum-deprived quiescent HL60. (A) Apoptosis induced by fenretinide in proliferating and quiescent HL60 cells, as evaluated by ApoAlert Annexin V kit and followed by flow cytometry. (B) Loss of mitochondrial transmembrane potential induced by fenretinide in proliferating and quiescent HL60 cells, as examined through rhodamine 123 and propidium iodide staining and followed by flow cytometry analysis. (C) ROS abundance induced by fenretinide in proliferating and quiescent HL60 cells, as detected by staining of the oxidation-sensitive fluorescent dye DCFH-DA.

The present invention is now further illustrated by providing the following examples. It shall be understood that the description in these examples are not intended to limit, in any way, the scope of the present invention, which should be only limited by the appended claims.

I. Methods and Materials

A. Leukemia Cell Lines, the Culture and the Drug Treatment

Leukemia cell lines include (a) CML-derived cell line K562 ($BCR-ABL^+$), (b) AML-derived cell lines NB4 and HL60. Cells were cultured in RPMI 1640 supplemented with 10% fetal bovine serum (PAA, Linz, Austria) at 37° C. in a humidified atmosphere with 5% CO2. Imatinib was kindly provided by Novartis Pharma (Basel, Switzerland) and fenretinide was purchased from Sigma (St Louis, Mo.). Cells were separately treated with (i) imatinib (0.25 µM), (ii) fenretinide (4 µM) or (iii) the combination of imatinib (0.25 µM) with fenretinide (4 µM) for 24, 48 and 72 hours.

B. Serum Deprived Quiescent Leukemic Cell Model

HL60 cells were cultured in RPMI 1640 supplemented (i) with or (ii) without 10% fetal bovine serum to obtain proliferating and quiescent leukemia cells respectively. Serum-deprived quiescent leukemic cells and proliferating leukemic cells were then cultured in media containing 0.5% FBS, and treated with 1 µM and 2.5 µM fenretinide, and also with chemotherapeutics as controls, 20 µM idarubicin (IDA) and 5 µM cytarabine (Ara-C).

C. $CD34^+$ Cell Isolation

Fresh bone marrow (BM) cells were obtained from 38 patients with CML and 5 non-leukemic donors, 25 AML, 17 ALL, and 8 normal specimens with informed consent according to the Declaration of Helsinki. Approval was obtained from Institutional Review Board at the School of Medicine in Shanghai Jiao Tong University. BM mononuclear cells were isolated by Ficoll density gradient centrifugation (Shanghai Second Reagent Factory, Shanghai, China). $CD34^+$ Cell were selected using EasySep® Human CD34 Positive Selection kit (Stem Cell Technologies, Vancouver, BC, Canada) according to the manufacturer's instructions. The purity of CD34 cells ranged between 92 and 98% in all samples detennined by flow cytometry. The $CD34^+$ cells were cultured in a serum-free medium (StemPro 34; Gibco BRL, Gaithersburg, Md.) supplemented with growth factors (PeproTech, London, United Kingdom) (20). The growth factors consisted of GM-CSF (200 pg/mL), G-CSF (1 ng/mL); SCF (200 pg/mL); LIF (50 pg/mL), MIP-1α (200 pg/mL) and IL-6 (1 ng/mL).

D. Apoptosis Assessments of Primitive Leukemic Stem and Progenitor Cells

Primitive AML and CML subpopulations ($CD34^+$ cells) were identified using CD34-PE in combination with CD38-APC, and followed by double-labeling with 7AAD and Annexin V antibodies for apoptosis assessment. The $CD34^+$ cells were first stained with antibodies against the surface markers CD34-PE and CD38-APC (Beckman Coulter, Fullerton, Calif.) and incubated at room temperature for 15 minutes. Cells were then washed with cold PBS and resuspended in 200 µL annexin V 1×binding buffer (10 mM HEPES/NaOH, pH 7.4, 140 mM NaCl, 2.5 mM CaCl2), 5 µL AnnexinV-FITC (BD Phanningen, San Diego, Calif.) and 7-aminoactinomycin (7-AAD, 0.25 mg/mL) (Molecular Probes, Eugene, Oreg.). Subsequently, the samples were incubated at room temperature for 15 minutes and analyzed by flow cytometry.

E. Apoptotic Assays of Cell Lines $2×10^5$ cultured cells were used for evaluating apoptosis using an ApoAlert Annexin V-FITC Apoptosis Kit (BD Biosciences). Cells were washed once by PBS, resuspended in 200 µl Annexin-V binding buffer, and then stained with Annexin V-FITC 5 µl, PI 10 µl for 15 min at room temperature in the dark. Cells were subsequently analyzed by flow cytometry.

F. Mitochondrial Transmembrane Potential (MTP) Assay

Loss of MTP was evaluated through rhodamine 123 (Rh123) and propidium iodide (PI) staining. $2×10^5$ cells were washed by PBS and incubated with 1 µg/ml Rh123 at 37° C. for 30 min. After washed by PBS, 10 µl PI was added to cells for 15 min at room temperature in the dark. Fluorescence emission at 530 nm (representing R123 retention as a function of MTP) was measured with flow cytometry.

G. Evaluation of ROS Accumulation

The intracellular generation of reactive oxygen species (ROS) was measured using of the oxidation-sensitive fluorescent dye 2,7-dichlorofluorescin diacetate (DCFH-DA) (Molecular Probes). After 3 h exposure of fenretinide, $2×10^5$ cells were harvested and washed once with PBS, then loaded with 1 ml PBS containing 10 µM of DCFH-DA. The cells were then incubated at 37° C. for 30 min and the fluorescence intensity was measured at 530 nm.

H. Western Blotting

Western blotting was preformed with caspase 3 (BD Phanningen, San Diego, Calif.), cleaved caspase-3, phospho-BCR-ABL, phospho-STAT5 and β-actin (Cell Signaling Technology, Beverly, Mass.), cleaved PARP and GADD153 (Calbiochem, SanDiego, Calif.), BCR-ABL and GRP78 (Santa Cruz, Calif.), NRF2 (Santa Cruz Biotechnology, Santa Cruz, Calif.), HSF1 (Santa Cruz Biotechnology, Santa Cruz, Calif.) antibodies on either total protein lysates or nuclear extracts.

I. Colony Forming Assays

The $CD34^+$ cells were separately mixed with imatinib (0.25 µM), fenretinide (2 µM and 4 µM) or the combinations of fenretinide (2 µM or 4 µM) with imatinib (0.25 µM). A quantity of 1000 $CD34^+$ cells were plated in semisolid methylcellulose-based media (Methocult H4434: Stem Cell Technologies, Vancouver, BC, Canada). After incubation at 37° C. in a fully humidified atmosphere of 5% CO2 for 14 days, granulocyte macrophage-colony-forming units (CFU-GM), erythroid burst-forming units (BFU-E), granulocyte, erythrocyte and monocyte, megakaryocyte-colony-forming units (CUF-GEMM) were counted. Only clusters with >50 cells were counted as a colony.

J. Cell Cycle Analysis

Cells were harvested and washed twice with phosphate-buffered saline (PBS), then fixed in ice-cold 75% ethanol. After overnight incubation at 4° C., cells were washed twice with PBS and re-suspended in 1 ml of PBS containing 10 µg/ml propidium iodide (PI) and 0.5 µg/ml RNaseA at 37° C. for 30 min. Cell cycle phase distribution were analyzed by flow cytometry, and the data were analyzed using cellFit software.

K. Statistical Analysis

Statistical analysis was performed using GraphPad Prism software (GraphPad Software, San Diego, Calif.). Data was analyzed by 1-way ANOVA followed by Tukey post hoc test. For two group comparisons, significance was determined by paired t tests.

L. Microarray Hybridization and Data Mining

Microarrays with 12,630 cDNA clones representing 10,647 genes were fabricated in-house by using a Generation III spotter (Amersham Pharmacia Biosciences). CDNA clones were sequence-verified and enriched with genes expressed in hematopoietic cells. Total RNA was prepared by usingTRIzol (Life Technologies), further purified with an RNEasy column (Qiagen), and quantified by using an RNA LabChip kit (Agilent Technologies, Palo Alto, Calif.) followed by reverse-transcription labeling. Approximately 30 µg of each RNA sample was reverse-transcribed into cDNA primed with oligo(dT) and labeled with either Cy3-dCTP or Cy5-dCTP by using Superscript II reverse transcriptase (Life Technologies). After hybridization under a standard protocol, data acquisition was performed by using a laser scanner (Axon Instruments, Union City, Calif.). The ratios of the reference control and the treated RNA samples were calculated from the normalized values. The threshold for conservative 2-fold changes of these ratios was used to determine regulated genes. To avoid artifacts while retaining the biologically meaningful genes inherent to microarray expression data, we have proposed a robust approach for gene selection and gene clustering, a modified method of component plane presentation (CPP) integrated self-organizing map (SOM) (Xiao et al., 2003) (Methods and system for analysis and visualization of multidimensional data. U.S. Pat. No. 6,897, 875).

M. Quantitative Real-Time RT-PCR

Real-time quantitative RT-PCR was preformed on ABI7900 thermocycler detection system using SYBR Green I (Applied Biosystems, Foster City, Calif.).

N. Antagonist Assays

For ROS antagonist assays, NB4 cells were pre-treated by 100 µM of antioxidant vitamin C (ascorbic acid sodium salt; Sigma) for 2 hours and followed by treatment of 1 µM fenretinide for 24 hours, and then subjected to apoptosis evaluation. For proteasome antagonist assays, NB4 cells were treated with 0.5 µM fenretinide and/or 0.2 µM of the proteasome inhibitor MG132 (Calbiochem) for 48 hours prior to apoptosis evaluation.

O. Immunofluorescence Microscopy Analysis

For cellular localization analysis, NRF2 and HSF1 were visualized by immunofluorescence microscopy.

P. Chromatin Immunoprecipitation Analysis

Chromatin immunoprecipitation (ChIP) was carried out using antibodies against NRF2 and HSF1. Immunoprecipitates were subjected to quantitative real-time PCR to validate potential (transcription factor binding sites) TFBSs in gene promoters computationally identified by integrative analysis of transcriptome data and genome sequences.

Q. Cell Viability Assay

The cell viability was determined by 3-(4,5-dimethylthiazol-2-yl)-2,5-diphenyltetrazolium bromide (MTT) assay.

II. Examples

Example 1

Serum-Deprived Quiescent Leukemic Cells, Modeled as the Leukemia Stem Cells, are More Sensitive to Fenretinide Previous reports show that AML-derived HL60 can be arrested after serum deprivation (Bello et al., 2005). To examine the effects of fenretinide on proliferating and quiescent leukemia cells, HL60 cells were chosen as serum deprived quiescent leukemic cell model obtained when incubated in RPMI 1640 without serum for 48 h, with G0/G1 phase cells (being in quiescent state) accounting up to 59.9%. Serum-deprived quiescent leukemic cells and proliferating leukemic cells were then cultured in media containing 0.5% FBS, and treated with 1 µM and 2.5 µM fenretinide, and also with chemotherapeutics as controls, 20 µM idarubicin (IDA) and 5 µM cytarabine (Ara-C). In proliferating HL60 cells, the percentage of apoptotic cells induced by 1 µM and 2.5 µM fenretinide for 24 h were respectively 11.8% and 36.8%, whereas the percentage reaches up to 39.5% and 52.7% for serum-deprived quiescent HL60 cells, indicating that serum-deprived quiescent leukemic cells are more sensitive to fenretinide-induced apoptosis, especially at 1 µM fenretinide ($p<0.0001$) (FIG. 1A). As comparisons, the apoptosis rates induced by chemotherapeutic drug IDA in proliferating and quiescent HL60 cells were 88.7% and 29.1% respectively, shown significantly reduced apoptotic effect on quiescent cells ($p<0.000001$). The similar results occurred in Ara-C treatments ($p<0.00001$). Fenretinide induces intracellular production of ROS, lowers mitochondrial transmembrane potential (MTP), and eventually leads to apoptosis in a variety of malignancies. We measured MTP induced by fenretinide in proliferating and quiescent HL60 cells, as examined through rhodamine 123 and propidium iodide staining and followed by flow cytometry analysis. Serum-deprived quiescent HL60 cells showed more significant reduced MTP than proliferating HL60 cells by fenretinide, whereas these quiescent cells showed little change in MTP by 20 µM IDA or 5 µM Ara-C (FIG. 1B). We further measured intracellular ROS abundance induced by fenretinide. We found that the cellular ROS level of quiescent cells decreased about 36% after serum deprivation for 48 h. After incubation with 1 µM and 2.5 µM fenretinide for 3 h, the ROS level of proliferating cells increased by 1.77 and 2.6 fold, respectively. For quiescent cells, the fold change of ROS was 3.83 and 4.3, respectively. Serum-deprived quiescent leukemic cells showed more significant ROS generation than proliferating cells exerted by fenretinide, not only with respect to the fold increase of ROS, but also with respect to the ultimate ROS level (FIG. 1C).

Example 2

Fenretinide Inhibits Colony Forming in Primary CML Cells

Figure 2:
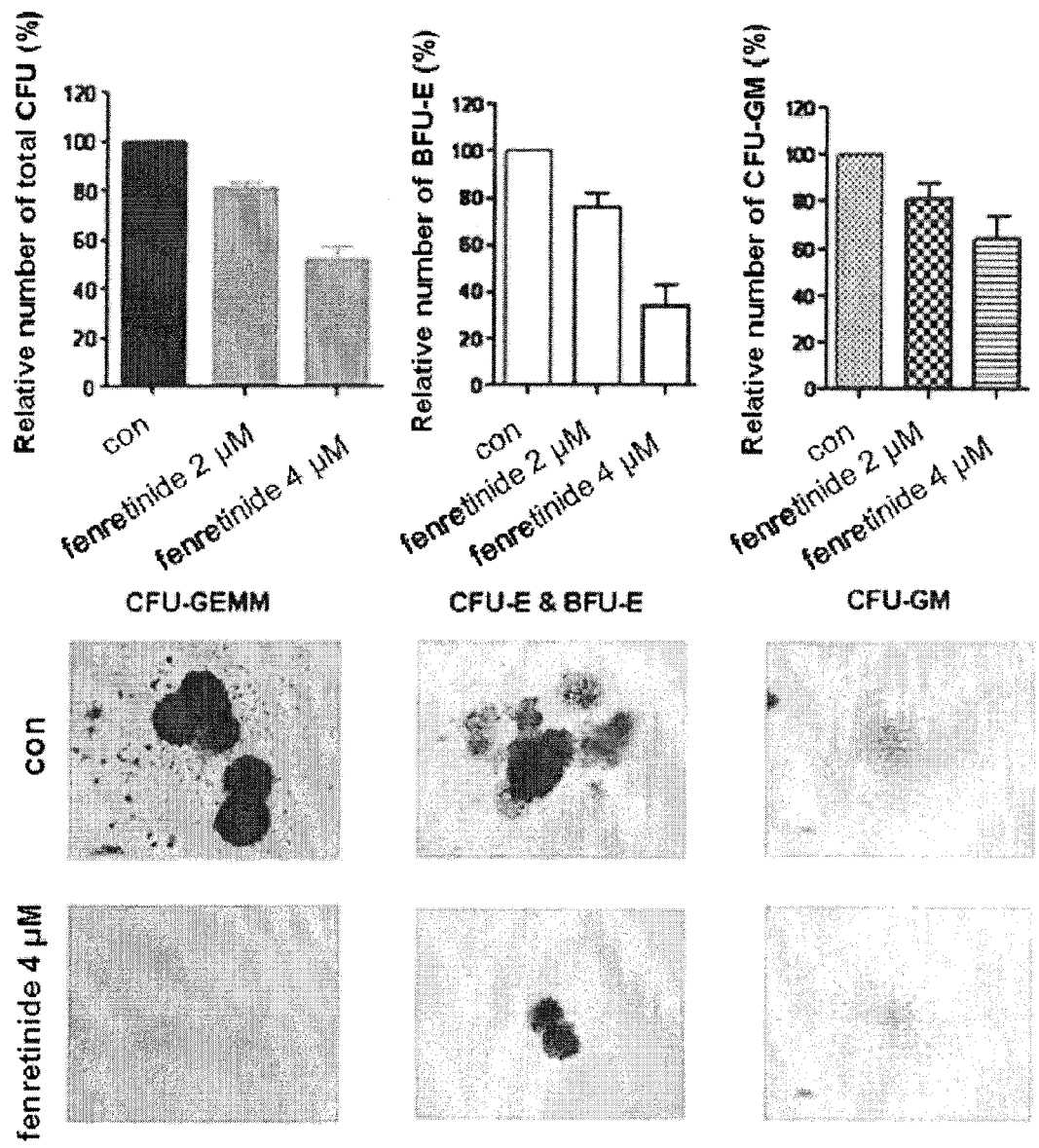
FIG. 2 shows effects of fenretinide on colony forming in primary CML cells. CML $CD34^+$ Cell isolated from bone marrow specimens of CML patients were plated in Methocult H4434 (Stem Cell Technologies), which mixed with 2 µM and 4 µM fenretinide, cultured for 14 days, and then subjected to progenitor colony assay, respectively for granulocyte macrophage-colony-forming units (CFU-GM), erythroid burst-forming units (BFU-E), granulocyte, erythrocyte and monocyte, megakaryocyte-colony-forming units (CFU-GEMM).

We further performed study to examine the effects of fenretinide on colony forming in primary CML cells derived from 38 bone marrow specimens of CML patients (TABLE 1). First, CML CD34$^+$ Cells were isolated using using Easy-Sep® Human CD34 Positive Selection kit (Stem Cell Technologies, Vancouver, BC, Canada). Upon treated with 2 μM and 4 μM fenretinide, colony forming assays were performed respectively on granulocyte macrophage-colony-forming units (CFU-GM), erythroid burst-forming units (BFU-E), granulocyte, erythrocyte and monocyte, megakaryocyte-colony-forming units (CFU-GEMM). As shown in FIG. 2, The number of BFU-E was significantly reduced when the concentration of fenretinide increased from 2 μM to 4 μM with the inhibition of 24%±6% to 66%±9% ($p<0.001$), whereas a slight decrease in the number of CFU-GM was observed when the concentration of fenretinide increased from 2 μM to 4 μM with the inhibition of 19%±17% to 36±9% ($p<0.05$). GFU-GEMM formed by the more primitive progenitor cells could not be detected in fenretinide treatments.

Example 3

Figure 3:
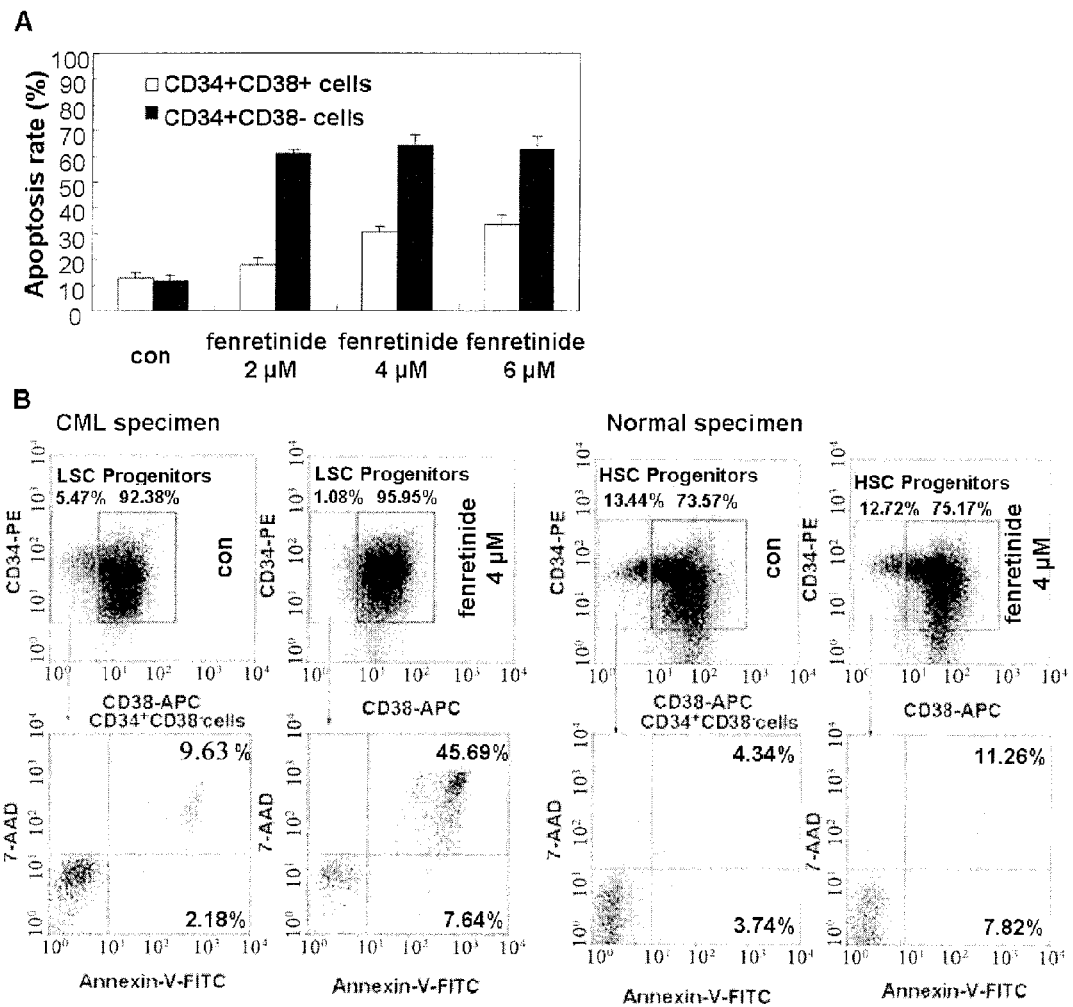
FIG. 3 shows that fenretinide preferentially targets more primitive CML stem and progenitor cells. (A) Fenretinide effectively induces apoptosis of $CD34^+CD38^-$ CML stem cells and $CD34^+CD38^+$ CML progenitor cells. (B) Fenretinide specifically targets CML stem cells, while sparing normal hematopoictic stem cells. CD34-PE and CD38-APC antibodies were utilized to analyze the subpopulations of the fenretinide-treated CML cells derived from bone marrow specimens of CML patients, CD34+CD38− enriched with CML stem cells, and CD34+CD38+ with CML progenitor cells. After gating on primitive CML subfractions, 7AAD and Annexin V antibodies were used to assess apoptosis. As a comparison, apoptosis-inducing effects of the fenretinide on normal hematopoietic stem cells (HSC) were similarly assessed.

Fenretinide Preferentially Targets More Primitive CML Stem and Progenitor Cells While Sparing the Normal Hematopoietic Stem Cells Populations of Leukemic cells have been demonstrated to be organized in a hierarchical fashion (Bonnet and Dick). It would be of significance to find out the subpopulations specifically targeted by fenretinide. We divided the CML patient specimens into mononuclear cells and $CD34^+$ cells. The $CD34^+$ CML cells are primitive cells including CML stem and progenitor cells. Upon treated with fenretinide, $CD34^+$ CML cells were further subdivided into $CD34^+CD38^-$ enriched with CML stem cells and $CD34^+CD38^+$ with CML progenitor cells. After gating on primitive CML subfractions, 7AAD and Annexin V antibodies were utilized for apoptosis assessment by FACS. The results demonstrated that fenretinide induced little apoptosis in mononuclear cells, and induced apoptosis of $CD34^+CD38^+$ cells in a dose-dependent manner (17.83%±6.01%, 30.60%±4.93%, 33.08%±19.43% at 2 μM, 4 μM and 6 μM respectively), whereas the CD34+CD38– cells had severe apoptosis even at a low dose of fenretinide (60.58%±2.76%, 63.75%±8.49% and 62.83%±9.72% at 2 μM, 4 μM and 6 μM respectively) (FIG. 3A). The difference of apoptosis rates between $CD34^+CD38^+$ and $CD34^+CD38^-$ cells was significant ($p<0.001$). The effects of the fenretinide exposures on the leukemia stem cells (LSC) and normal hematopoietic stem cells (HSC) in the $CD34^+CD38^-$ cells were shown in a representative specimen (FIG. 3B). The specimens in 5 CML patients had the similar effects on the LSC and in 5 non-leukemic donors had the similar patterns as that of nonnal HSC. The LSC in the $CD34^+CD38^-$ cells treated with fenretinide were markedly reduced with 80.3%. The apoptosis in the LSC was also significantly induced by fenretinide (53.3%) compared to that of the untreated cells ($p<0.001$). However, the toxicity in normal HSC induced by fenretinide was extremely low with almost no change in the cell proportion (5.36%) and little apoptosis (19.08%). These results demonstrated that fenretinide could specifically target the CML stem and progenitor cells with sparing the normal hematopoietic stem cells.

Example 4

Figure 4:
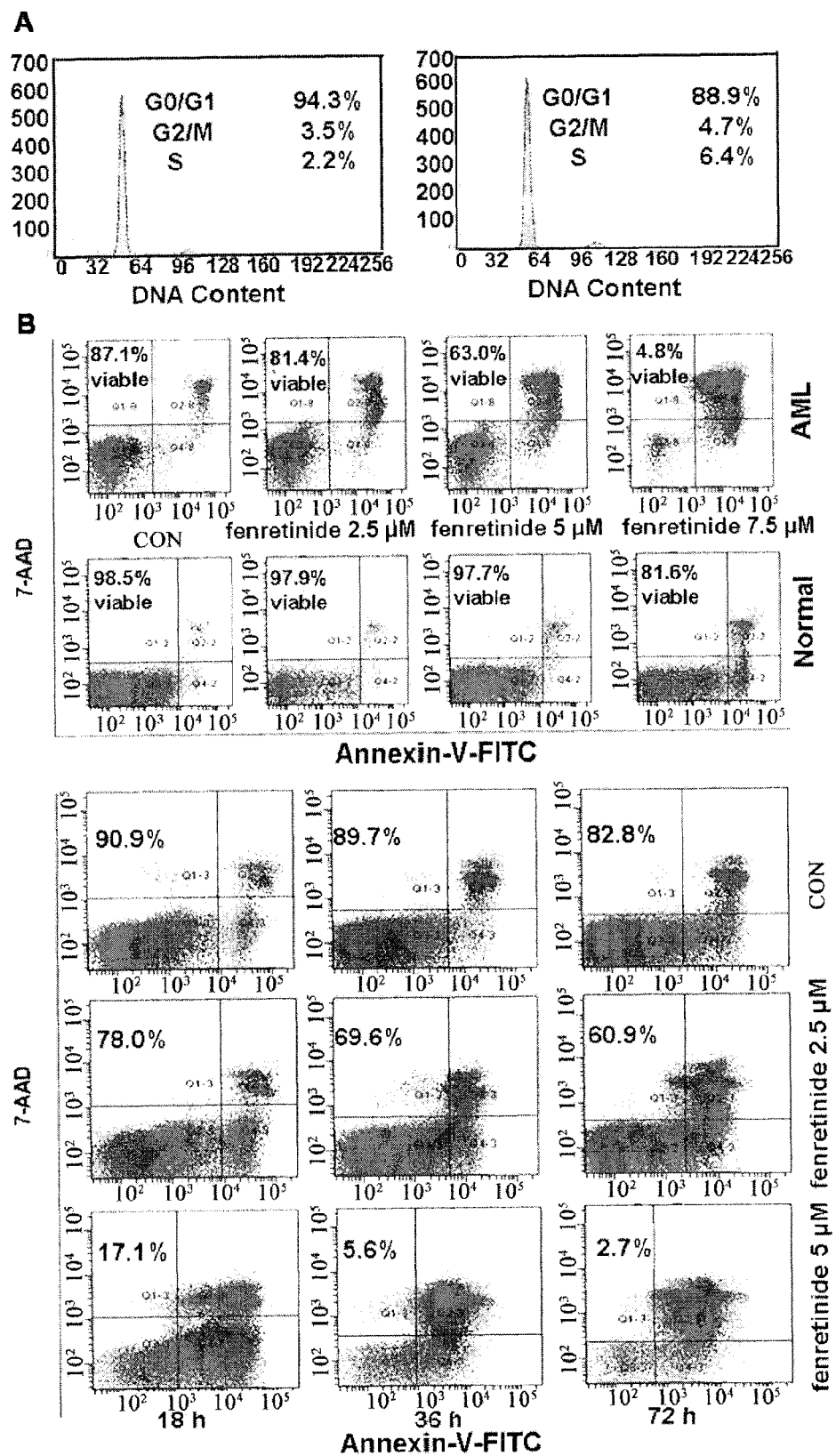
FIGS. 4A and 4B show that fenretinide induces robust apoptosis in quiescent primary acute leukemia specimens including AML and ALL. (A) Cell-cycle profiles of leukemia CD34+ specimens. (B) Apoptosis profiles of AML CD34+ cells and normal CD34+ cells induced by fenretinide.

Fenretinide Induces Robust Apoptosis in Quiescent Primitive Acute Leukemia Specimens Including AML and ALL, While Sparing Normal Counterparts Primary acute leukemia cells from specimens including AML and ALL are mostly quiescent, especially for the subpopulations of leukemic $CD34^+$ cells (Guan and Hogge, 2000). To verify if this quiescent leukemia cells are sensitive to fenretinide, we compared the effects of fenretinide on primary leukemia versus normal specimens during short-term suspension culture. $CD34^+$ cells were isolated from primary acute leukemia specimens, and subjected to DNA content analysis through propidium iodide staining and followed by flow cytometry. The majority of isolated $CD34^+$ cells from AML and ALL were in G0/G1 phase of the cell cycle, indicating the quiescent feature of leukemia $CD34^+$ cells (FIG. 4A). Then, apoptosis profiles of AML $CD34^+$ cells and normal $CD34^+$ cells were examined through annexin-V FITC and 7AAD double staining (FIG. 4B). Fenretinide potently induced robust apoptosis in a time- and dose-dependant manner. The apoptosis-inducing effects of fenretinide on AML $CD34^+$ cells were significantly increased, with the increase of fenretinide concentration and with the increase of incubation time. In contrast, normal hematopoietic $CD34^+$ cells were relative resistant to fenretinide.

TABLE 2 showed the effects of fenretinide treatment on 25 AML, 17 ALL, and 8 normal specimens in $CD34^+$ populations. At 5 μM fenretinide, the mean viability of AML $CD34^+$ cells was 45.4% after 18 h in culture. However, the response of AML specimens to fenretinide was heterogeneous, with the viability of most sensitive to be 0.5% (AML #20), and the most resistant to be 89.7% (AML #8). The mean viability of AML $CD34^+$ specimens was reduced to 12.2% by increasing fenretinide to 7.5 μM. Similarly, ALL $CD34^+$ cells also showed a strong apoptotic response to fenretinide, with mean viability to be 58.0% (5 μM) and 20.9% (7.5 μM), respectively. To verify the specificity of fenretinide for malignant cells, viability of normal hematopoietic cells was determined. Our studies found normal hematopoietic $CD34^+$ cells showed almost no decrease in viability when treated with 5 μM fenretinide (97.1%), and a decrease in viability at 7.5 μM fenretinide (58.1%). So we presumed that the safe dose of fenretinide should below 5 μM. Compared with normal $CD34^+$ cells, fenretinide shows specifically target AML and ALL $CD34^+$ cells.

Figure 5:
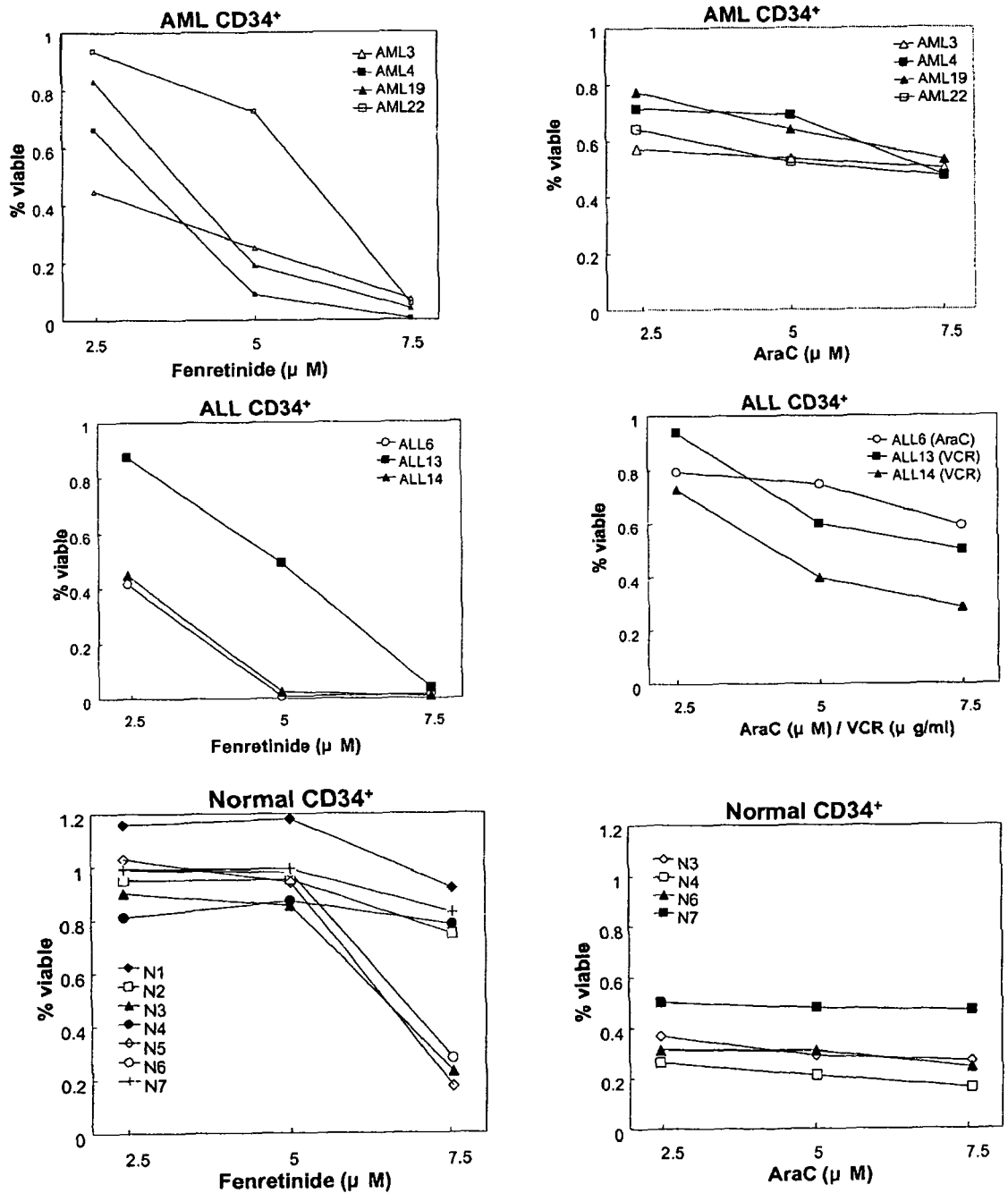
FIG. 5 shows that fenretinide preferentially targets more primitive acute leukemia stem and progenitor cells. CD34-PE and CD38-APC antibodies were utilized to analyze the subpopulations of the fenretinide-treated acute leukemia cells derived from bone marrow specimens of AML and ALL patients, CD34+CD38− enriched with acute leukemia stem cells, and CD34+CD38+ with acute leukemia progenitor cells. Annexin-V FITC and 7-AAD of the gated primitive acute leukemia subfractions were profiled to assess apoptosis-inducing effects of fenretinide on leukemia stem and progenitor cells.

Furthermore, we examined whether fenretinide can preferentially target highly quiescent LSCs with $CD34^+CD38^-$ immunophenotyte and leukemia progenitor cells with $CD34^+CD38^+$ for AML and most ALL specimens. Due to the difficulty of obtaining adequate normal $CD34^+CD38^-$ cells, our apoptosis data of normal specimens came from $CD34^-$ cell populations. Also, we used Ara-C and VCR (vincristine) as controls to test the apoptosis of leukemia stem cells, which were thought to be resistant to these chemotherapeutics. Our results showed that Fenretinide induced more apoptosis in $CD34^+CD38^-$ acute leukemia stem population than $CD34^+CD38^+$ acute leukemia progenitor population, while sparing normal $CD34^+$ cells (FIG. 5).

Example 5

Figure 6:
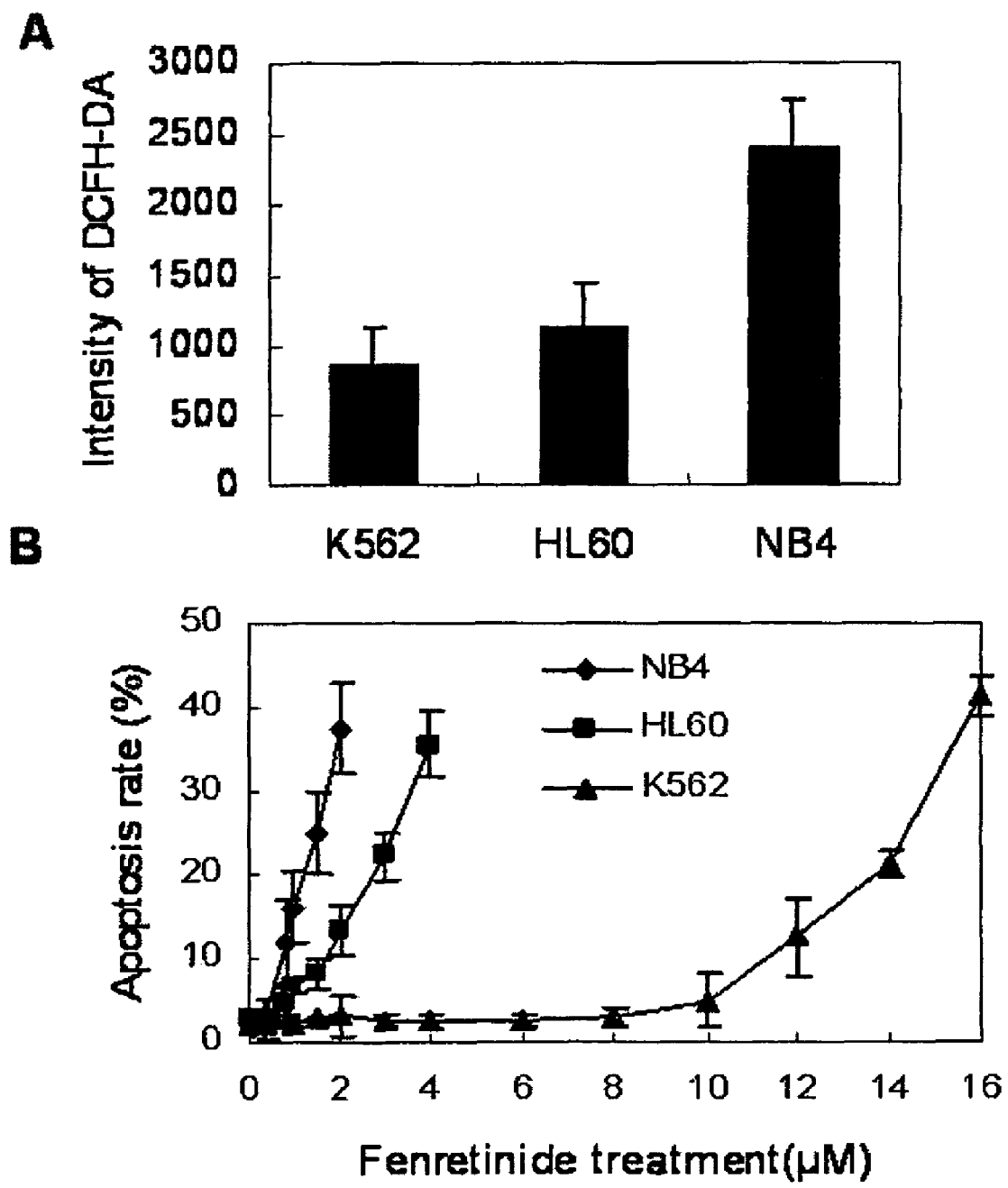
FIGS. 6A and 6B show that fenretinide-induced apoptosis is well correlated with intracellular ROS levels in the leukemia cell lines. (A) The ROS level in K562, HL60 and NB4 leukemia cell lines, as evaluated by DCFH-DA staining. (B) Sensitivity of K562, HL60 and NB4 leukemia cell lines to fenretinide. Apoptosis rates were examined through annexin-V FITC and 7AAD double staining.

Fenretinide-Induced Apoptosis is Well Correlated with Intracellular ROS Levels in the Leukemia Cell Lines Fenretinide induces ROS-dependent apoptosis is the common feature in a variety of tumors (Sun et al., 1999). Here, we extensively explored the relationship between intracellular ROS levels and apoptosis outcomes induced by fenretinide in a panel of leukemia cell lines, including K562, HL60 and NB4. The intracellular ROS levels in leukemic cells were evaluated by DCFH-DA staining, and apoptosis of leukemic cells induced by fenretinide treatment with a series of concentrations was examined through annexin-V FITC and 7AAD double staining. We found that intracellular ROS level in leukemia lines was ordered as NB4, HL60, and K562 in a descend manner (FIG. 6A). Interestingly, their susceptibilities to fenretinide-induced apoptosis were unanimously positively correlated with levels of intracellular ROS (FIG. 6B).

Example 6

Figure 7:
FIGS. 7A and 7B and 7C and 7D show that fenretinide can enhance genes related to oxidative stress and endoplasmic reticulum (ER) stress at the molecular level in the leukemia cell lines. (A, B) The expression patterns of genes involved in oxidative stress-mediated apoptosis in NB4 cells with fenretinide treatment, as identified by microarray analysis and Western blotting analysis. (C) Major functional features associated with ER stress in fenretinide-treated K562 cells, as identified by microarray analysis. (D) The splicing of the XBP-1 gene (ER stress marker) in K562 cells with the fenretinide treatment, as analyzed by RT-PCR.

Prominent Molecular Events Underlying Fenretinide-Induced Apoptosis in Leukemia Cell Lines, and Therapeutic Implications of Synergistic Apoptosis Induction Using Fenretinide and Proteasome Inhibitor Despite of tremendous efforts (Oridate et al., 1997), mechanisms underlying fenretinide-induced apoptosis are far from clear. In particular, knowledge in terms of how oxidative stress is converted into downstream activities in fenretinide-treated cancer cells is limited. We performed a comprehensive analysis of fenretinide-induced apoptosis in leukemia cell lines through microarray technology integrated robust data mining tool, and techniques of molecular biology. Transcriptome analysis of fenretinide-induced apoptosis in NB4 cells highlighted numerous stress-responsive events at the temporal-spatial level, typifying a process of oxidative stress-mediated apoptosis. Among these prominent events were genes involved in transcriptional regulation, ribosome machinery, oxidative stress, endoplasmic reticulum stress/unfolded protein response (UPR), ubiquitin-proteasome system and apoptosis (FIG. 7A). Similarly, transcriptome profiling of fenretinide-induced apoptosis in K562 cells revealed that those regulated genes were mainly involved in ER stress, UPR and proteasome (FIG. 7C). Recently, data have shown that fenretinide may perturb cellular homeostasis and induced ER stress, which may eventually contribute to apoptosis. ER stress is cellular defense mechanism responding to various stimuli including oxidative stressors. To validate this notion and molecular events revealed by transcriptome analysis, we further confirmed the involvement of ER stress by quantitative real-time RT-PCR of ER stress marker XBP-1. The splicing of the XBP-1 gene was observable in whole time courses of fenretinide-treated K562 cells (FIG. 7D).

Figure 8:
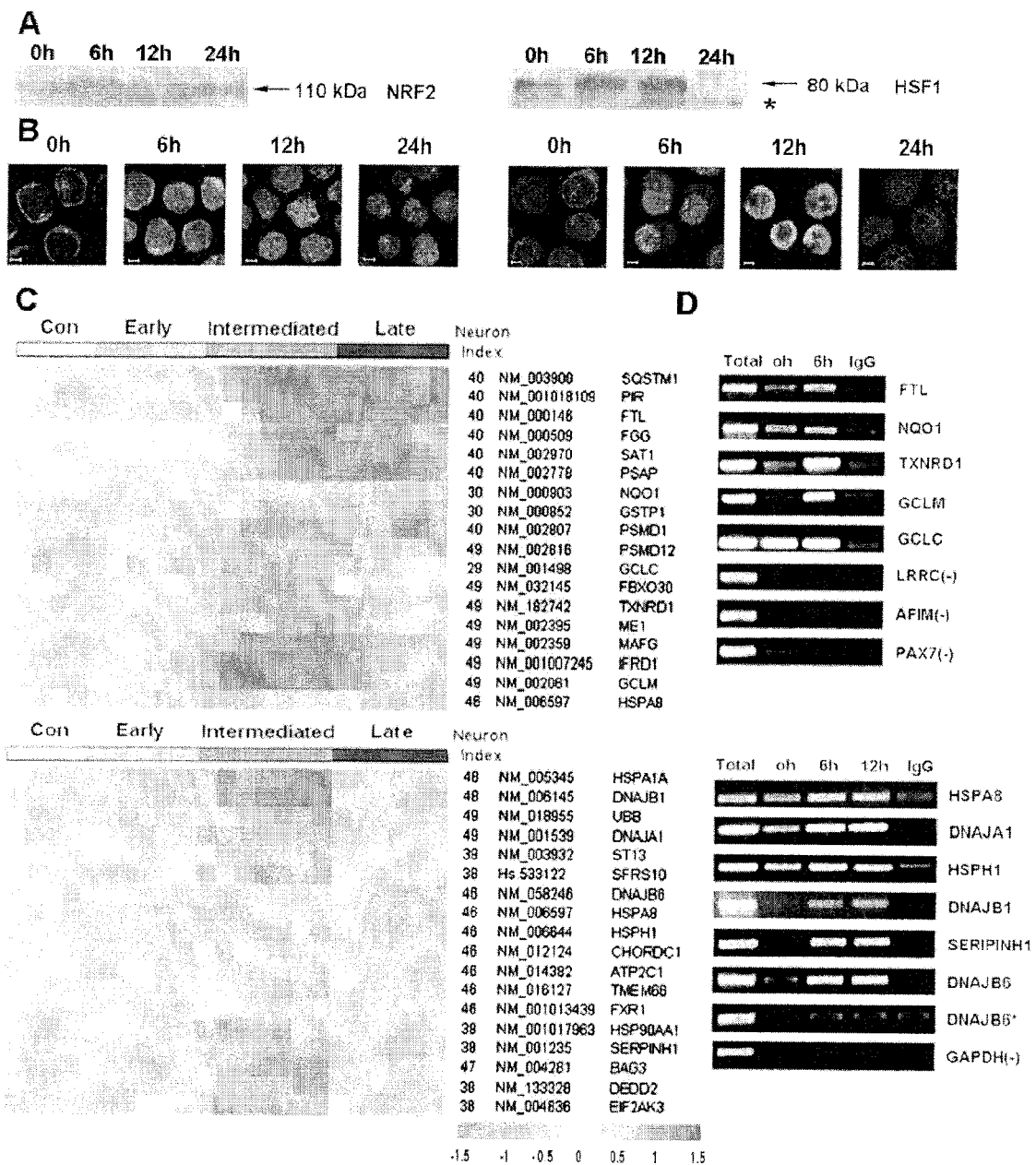
FIGS. 8A and 8B and 8C and 8D show coordinated regulation of stress-responsive transcription factors NRF2 and HSF1, and their target genes during the fenretinide-induced apoptosis in leukemic NB4 cells. (A) Western blot analysis of NRF2 and HSF1 from nuclear extracts of NB4 cells untreated or treated with 1 μM fenretinide at the indicated time points. "*" indicates the non-specific binding band. (B) Nuclear translocation of NRF2 and HSF1 following 1 μM fenretinide treatment in NB4 cells, as visualized by immunofluorescence microscopy (scale bars, 5 μm). (C) Illustration of expression patterns of genes potentially targeted by NRF2 and HSF1, respectively illustrated on the left and right panel. (D) Chromatin immunoprecipitation (ChIP) combined with PCR assays for the validation of physical interaction between transcription factors (i.e., NRF2 and HSF1) and their target genes. Total: total input; IgG: ChIP reaction with IgG antibody as a control; DNAJB6*: primers designed from non-TFBS region of the gene DNAJB6.

Transcriptome analysis of fenretinide-induced apoptosis in leukemia cell lines facilitated in-depth mining of biological information relevant to oxidative stress-mediated apoptosis, including the prediction of upstream transcription factors potentially involved in gene regulation. Of several dozens of transcriptional regulators predicted, stress-responsive transcription factors NRF2 and HSF1 are of particular interest for understanding how oxidative signaling is translated into downstream effects. NRF2 is known as a key regulator of intracellular redox balance, activating genes encoding anti-oxidative proteins under oxidative stress (Jaiswal, 2004; D'Autreaux and Toledano, 2007). Although HSF1 is commonly recognized as a heat-shock motivated transcription factor (Hayashida et al., 2006), it can also be activated by oxidative stress under certain circumstances (Ahn and Thiele, 2003). We therefore further investigated the temporal abundance and spatial localization of there two stress-responsive transcription factors during fenretinide-induced apoptosis in NB4 cells. As demonstrated in FIG. 8A, protein levels of both NRF2 and HSF1 were markedly elevated in nuclear extracts within 6 hours of exposure to fenretinide, and their temporal abundance was differentiated thereafter. The induction of NRF2 was extended beyond the 24 hour whereas HSF1 induction was terminated at this time point. Similarly, immunofluorescence microscopy analyses revealed a diffused distribution of NRF2 and HSF1 in untreated cells, and marked accumulation of both factors in nuclei of cells treated with fenretinide for 6 hours (FIG. 8B). Also, nuclear gathering of NRF2 was sustained beyond the 24 hour treatment whereas that of HSF1 was terminated. Moreover, the temporal-spatial changes of NRF2 and HSF1 were well in accordance with regulatory patterns of their potential target genes (FIG. 8C). Up-regulated expression of NRF2 potential target genes was extended to the late stage, whereas gene expression of HSF1 potential targets was unanimously terminated by the end of the intermediate stage. To explore whether NRF2 and HSF1 are physical bound to their targets as predicted above, we conducted chromatin immunoprecipitation (ChIP) assays using antibodies against NRF2 or HSF1. Based on the predicted TFBS of the representative genes listed in FIG. 8C, specific PCR primers were designed using ChIP products of either NRF2 or HSF1 as DNA templates. As illustrated in the left panel of FIG. 8D, genes with the predicted TFBS of NRF2 (i.e., FTL, NQO1, TXNRD1, GCLM and GCLC) are positive for NRF2 ChiP products, whereas unrelated genes (i.e., LRRC, AFIM and PAX7) are negative in the same products. Although a basal level of NRF2 binding was observed in untreated ChIP products, most of the predicted genes revealed significantly stronger signals in treated samples. Likewise, ChIP-PCR assays of HSF1 revealed similar results (the right panel of FIG. 8D). Of note, primers designed from the TFBS region revealed prominent bands in HSF1 ChIP products, whereas those from the non-TFBS regions of the same genes revealed absent signals (e.g., DNAJB6 vs. DNAJB6*). Altogether, our evidence indicates that NRF2 and HSF1 are activated upon ROS accumulation by the end of the early stage, converting oxidative signaling into downstream effects by directly acting on their target genes. NRF2 activation extends to the late stage while HSF1 activity is terminated by the end of the intermediate stage.

Figure 9:
FIG. 9 shows prominent impact of NRF2 and HSF1 on transcriptome signatures underlying oxidative stress-mediated apoptosis in leukemic NB4 cells. Stress-related expression data were assembled and displayed through hierarchical clustering. Transcription factor binding site (TFBS) information for each transcription factor is integrated on the left of the display, with putative hits marked in red. Various stress conditions are indicated at the top of the display. Except for apoptosis induced by fenretinide, these stress responses were all induced below the threshold where significant lethality occurred, possibly representing transcriptomic responses relevant to cell survival. Heat shock was induced in HeLa, fibroblast and K562 cells. Endoplasmic reticulum stress was induced in HeLa cells with the glycosylation inhibitor tunicamycin or thiol reducing agent DTT, and in fibroblasts with DTT. Oxidative stress was induced in HeLa cells with hydrogen peroxide ($H_2O_2$) or with menadione, and in fibroblasts with menadione.

Fenretinide-induced apoptosis in leukemic cells occurs in response to oxidative stress, and is orchestrated by stress-responsive transcription factors, as highlighted by the modulation of a large number of stress-responsive genes. We speculated that these stress-responsive genes might represent a signature spectrum characteristic of leukemia cells undergoing oxidative stress-mediated programmed cell death rather than survival upon stress stimulus. To validate this assumption, and to evaluate the potential impact of NRF2 and HSF1 on the assumed signature spectrum, we comparatively these stress-responsive genes with ATO-induced apoptotic expression data (Zheng et al., 2005) and several sets of expression data relevant to various stress responses under non-apoptotic conditions (Murray et al., 2004). Through hierarchical clustering of those overlaps, and followed by integration of genomic TFBS information, stress-responsive transcriptome features under apoptotic or non-apoptotic conditions were displayed (FIG. 9). By comparing these features across all the conditions, the assumed signature spectrum of this setting can be further partitioned into four categories (I-IV). Modulation of genes in category I is attributed largely to HSF1 activation, as also indicated by prominent up-regulation under heat shock. Of note, HSF1 activation under these non-apoptotic heat shock conditions appears to be sustained rather than transient. Modulation of genes in category II appears to be more complex, probably because they are orchestrated by multiple stress-responsive transcription factors such as CHOP and XBP1, as implicated by the observed multifaceted TFBS composition. Our data suggest that this gene category is also involved in the ER stress/UPR occurring at the intermediate stage of oxidative stress-mediated apoptosis, based on expression patterns as well as functional annotations.

Genes in category III are those directly involved in redox signaling during the intermediate and late stages, as highlighted by significant enrichment of NRF2 and its co-factor MAF. Activation of genes encoding subunits of the proteasome apparatus is one of the most prominent features in this study. These genes are unexceptionally clustered in category IV. TFBS analysis implicates that genes in this category are modulated by ELK1. Taken together, our data clearly show that stress-relevant transcriptome features of fenretinide-treated NB4 cells can be recognized as a signature spectrum characteristic for oxidative stress-mediated apoptosis in leukemia cells ROS signaling may represent an essential stimulus at the early stage of fenretinide-induced apoptosis. To provide further evidence for the dependency of ROS signaling, we preformed an antagonist assay using vitamin C as the antioxidant. As shown in FIG. 10A, vitamin C treatment completely abrogated fenretinide-induced apoptosis in NB4 cells.

Genes encoding components of proteasome were significantly up-regulated during fenretinide-induced apoptosis. Thus, we hypothesized that proteasome activity might function as a defense mechanism coupled to the UPR for unfolded/misfolded protein degradation to reduce the ER stress burden (Meusser et al., 2005). Accordingly, proteasome activation may antagonize the pro-apoptotic/apoptotic cascade. To explore this hypothesis, we used a proteasome inhibitor MG132 to block proteasome activities during fenretinide-induced apoptosis. As shown in FIG. 10B, a sub-cytotoxic concentration (0.2 µM) of MG132 together with a low dose of fenretinide (0.5 µM) indeed induced a significant amount of cell apoptosis within 48 hours, demonstrating synergistic rather than antagonistic effects of the two compounds.

Example 7

Figure 11:
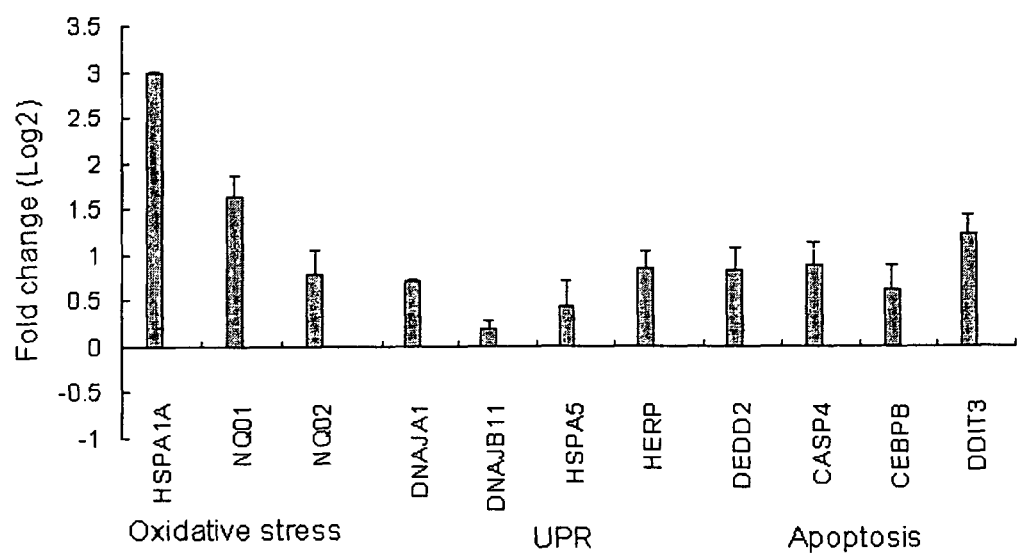
FIG. 11 shows that fenretinide can induce expression of genes involved in the oxidative and ER stress in CD34+ cells isolated from bone marrow specimens of primary CML patients, as preformed by real-time quantitative RT-PCR.

Fenretinide Enhances Genes Related to Oxidative Stress and Endoplasmic Reticulum (ER) Stress in CML CD34+ Cells Fenretinide preferentially targets more primitive leukemia stem and progenitor cells (Example 3 and Example 4), and mechanisms are involved in ROS-dependent apoptosis in a panel of leukemia cell lines. Additionally, the process of fenretinide-induced apoptosis is modulated by a large number of oxidative and ER stress genes (Example 5 and Example 6). It is of significant value to further evaluate whether fenretinide exerts similar mechanism on primitive leukemia stem and progenitor cells. Thus, we isolated CD34+ cells from CML patients, which were subjected to real-time quantitative RT-PCR for oxidative and ER stress genes identified based on microarray analysis of fenretinide-treated K562 cells. As illustrated in FIG. 11, genes involved in oxidative and ER stress were highly up-regulated in fenretinide-treated CML CD34+ cells, suggesting that these genes may serve as pharmacological targets of fenretinide intervention.

Example 8

Figure 12:
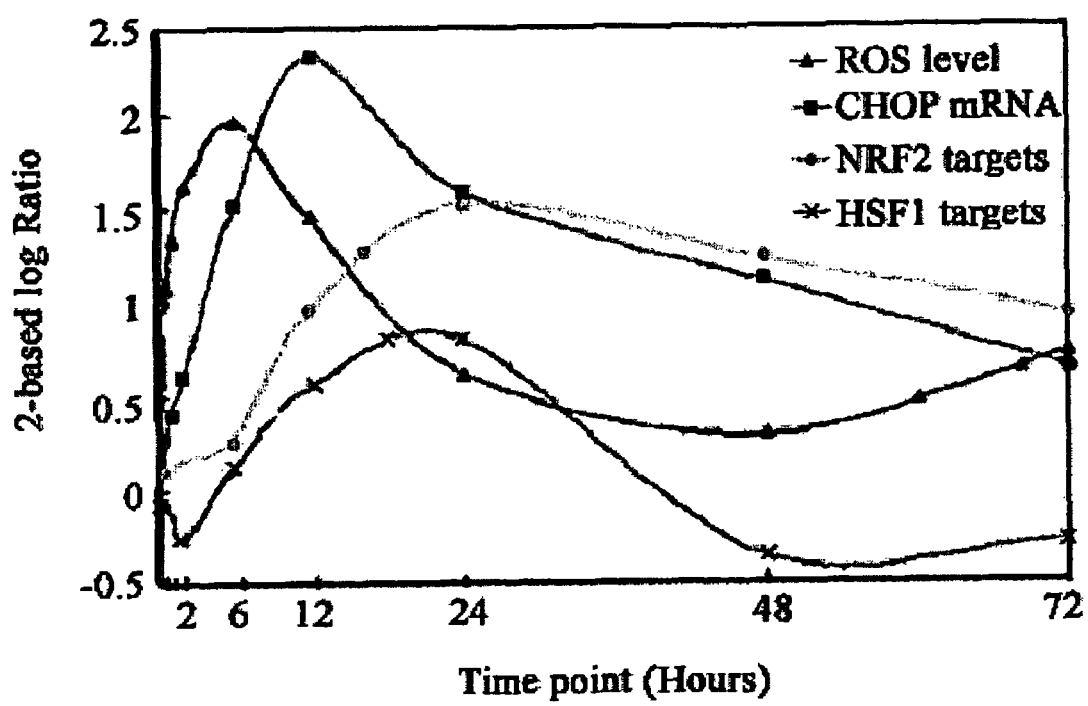
FIG. 12 shows dynamics of intracellular ROS level, pro-apoptotic CHOP mRNA, and expression pattern of NRF2-regulated-oxidative-stress genes and HSF1-regulated-ER-stress genes during fenretinide-induced apoptosis

Summary of Dynamic Changes of Coordinated Events Occurring During Fenretinide-induced Apoptosis Here we explored relevant events with temporal relationships during fenretinide-induced apoptosis. As shown in FIG. 12, changes of intracellular ROS are more complex than previously recognized, displaying left-skewed bell-shape curve (in blue). As expected, ROS accumulates sharply, reaching peak at 6 hour, and then unexpectedly decreases afterward gradually to the level roughly equal to two fold changes compared to the basal level of untreated control. The accumulation of ROS at the early stage (within 6 hours) not only accounts for the biological mechanism of fenretinide, but also incurs the stress-responsive events, as highlighted by activation of stress-responsive transcription factors NRF2 and HSF1 and the subsequent modulation of a large number of NRF2-regulated-oxidative-stress targets (curve in cyan of FIG. 12) and HSF1-regulated-ER-stress targets (curve in dark purple of FIG. 12). Although these two sets of stress-responsive genes are individually considered as regulators of cellular defense mechanisms, their coordinated regulation in such manner as consistent activation of NRF2 targets and transient activation of HSF1 targets can be critical for the effective progression of pro-apoptotic CHOP activities (curve in light purple of FIG. 12) in response to fenretinide stimuli.

Example 9

Synergistic Inhibition of AML Cell Proliferation Upon the Combination of Fenretinide and Ara-C Heterogeneous AML cells are organized in a hierarchical fashion, comprising of quiescent AML stem/progenitor subpopulation and proliferating leukemic blasts. To overcome resistance of conventional chemotherapeutic regimens like Ara-C and to prevent the occurrence of relapse, combination strategies involving the preferential ability of fenretinide to target more primitive stem/progenitor cell while sparing normal compartment and the well-known effect of Ara-C in killing proliferating cells can provide more effective and more efficient treatment for AML. Thus, we performed studies to determine the synergistic effects of fenretinide and Ara-C in AML cells.

Figure 13:
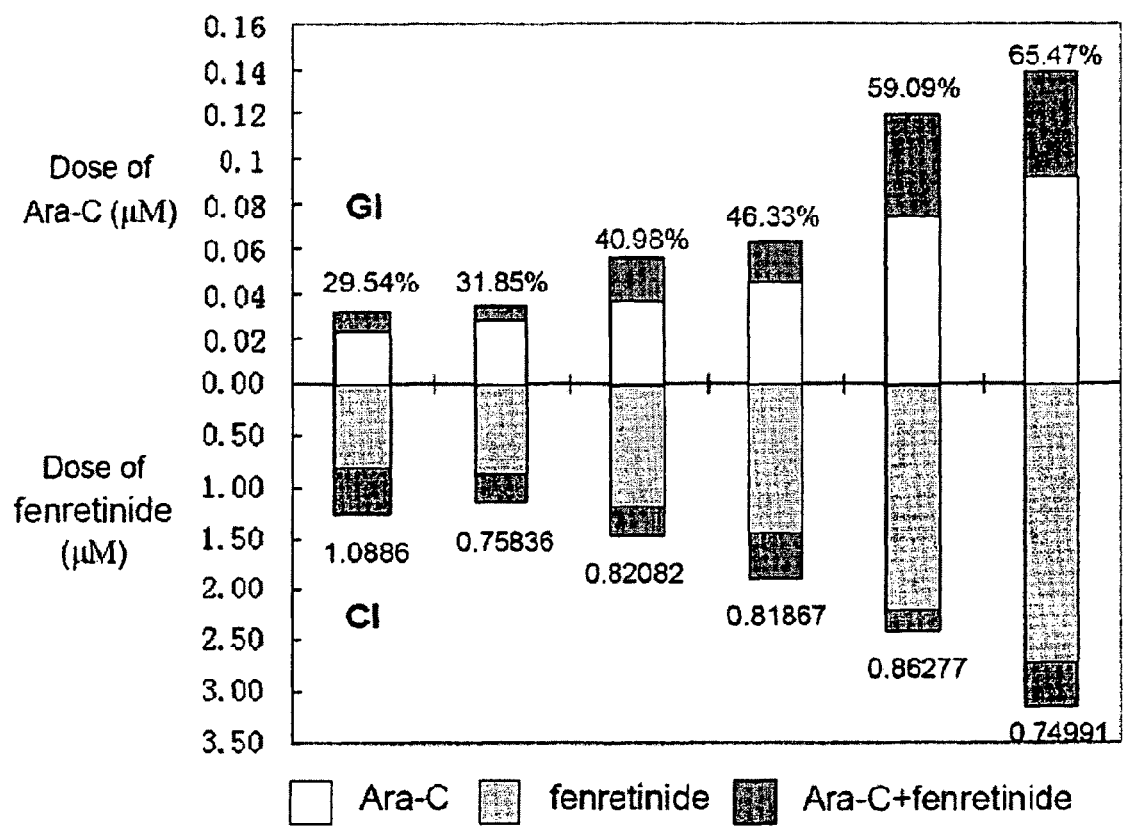
FIG. 13 shows effects of fenretinide and Ara-C on growth inhibition in AML. Distinctive doses (y-axis) of fenretinide, Ara-C and their combination produce the indicated growth inhibition (GI) and its corresponding combination index (CI).

The combination Index (CI) was used to test the combination effect of fenretinide and Ara-C on growth inhibition in AML cell line U937. The CI was calculated according to the classic isobologram equation: CI=d1/D1+d2/D2. In this equation, D1 and D2 represent the doses of drug 1 and drug 2 alone, required to produce x % effect, and d1 and d2 are the doses of drugs 1 and 2 in combination required to produce the same effect. And CI<1, CI>1 and CI=1 represent the synergism, additivity and antagonism, respectively. As FIG. 13 shown, when the growth inhibition rate was more than 30%, the CIs were all less than one, which means the combination of fenretinide with Ara-C had synergistic effect. For example, when the growth inhibition rate was 65.47%, the dose of fenretinide and Ara-C alone should reach respectively 2.72 µM and 0.091 µM, while the doses in combination of fenretinide and Ara-C were only 0.5 µM and 0.05 µM, respectively. Combination of fenretinide with Ara-C demonstrates remarkably synergistic effects and low toxicity. Undoubtedly, such combination strategies can provide a paradigm for improving conventional chemotherapies through specifically ablating the primitive hematologic cancer stem/progenitor cells by fenretinide.

Example 10

Effects of Fenretinide Combined with Imatinib on Inhibition of Colony Forming in Primary CML Cells, and Their Targets in CML Stem and Progenitor Cells, and Their Effects on BCR-ABL Activities in K562 Cells Understanding the molecular basis of CML, characterized by the oncogenic BCR-ABL fusion protein, has led to the development of highly effective targeted drug imatinib (ST1571, Gleevec) that block BCR-ABL tyrosine kinase activity. Treatment with imatinib has allowed patients with CML to experience nearly 87% of complete cytogenetic response (CCR) (Druker et al., 2006). However, many patients have eventually developed resistance and disease relapse to this treatment. On the one hand, it is often due to BCR-ABL mutations, which effect the binding of imatinib (Shah et al., 2002). On the other hand, the link between inactivation of BCR-ABL kinase activity and induction of apoptosis in the most primitive CML cells remains unclear. The persistence of BCR-ABL positive cells in almost all the patients treated with imatinib therapy suggests that inhibition of the BCR-ABL kinase activity alone can not eradicate all of the CML cells, especially CML stem cells (Graham et al., 2002). In the present invention, we demonstrate that new treatment such combination strategies involving imatinib and fenretinide can overcome imatinib resistance and the disease relapse. Further studies were performed to determine the synergistic effects of fenretinide with imatinib on the CML patient specimens as well as their synergistic mechanisms based on K562 cell line model.

Figure 14:
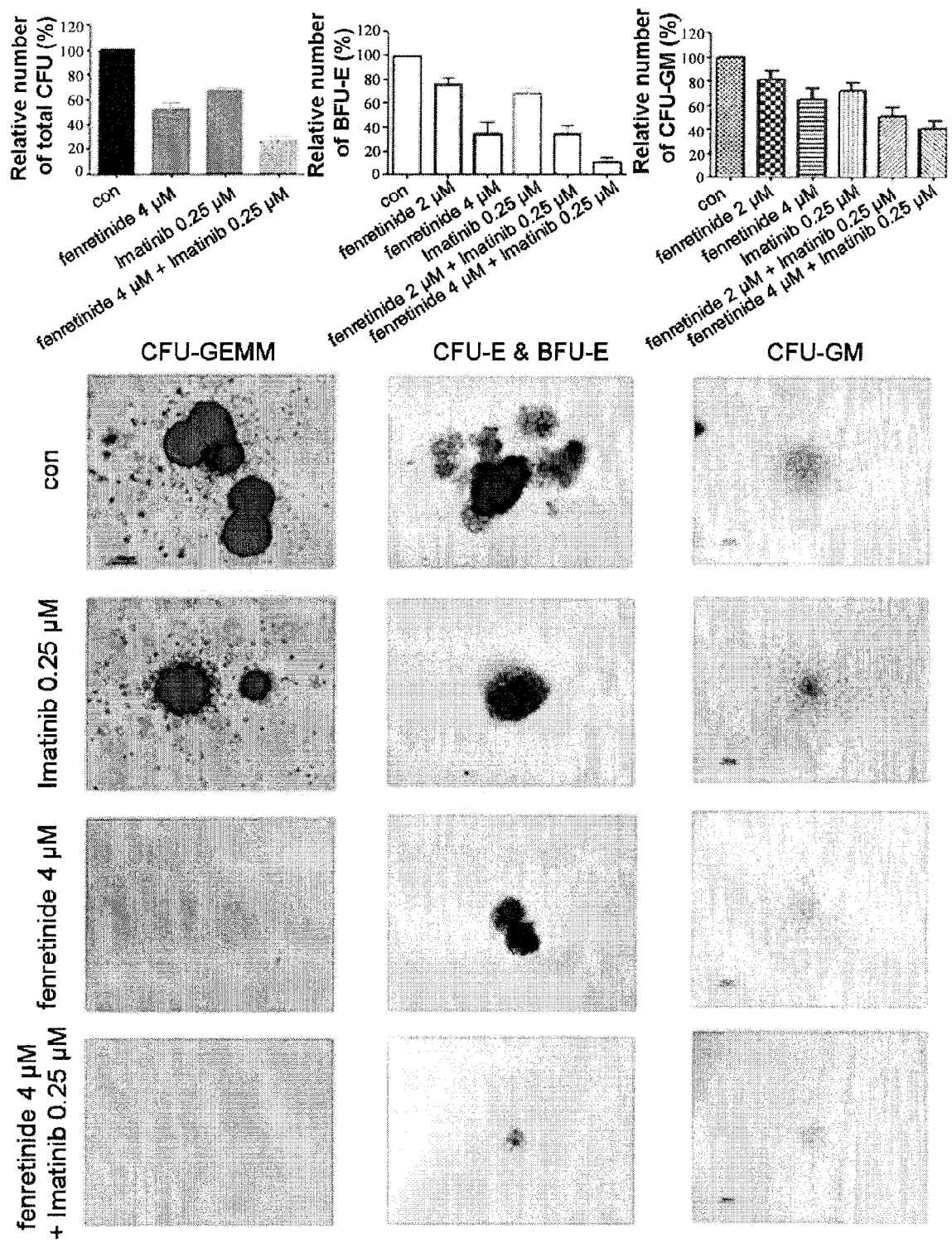
FIG. 14 shows effects of fenretinide and imatinib on colony forming in primary CML cells derived from bone marrow specimens of CML patients. CML CD34+ cell isolated were plated in Methocult H4434 (Stem Cell Technologies), which separately mixed with 0.25 μM imatinib, 4 μM fenretinide, or the combinations of 4 μM fenretinide with 0.25 μM imatinib, cultured for 14 days, and then subjected to progenitor colony forming assay, respectively for CFU-GM, BFU-E, and CFU-GEMM.

As shown in Example 2, fenretinide can effectively inhibit the formation of more primitive progenitor CML cells. Thus, we also examined the effects of imatinib and the co-treatment with fenretinide on colony forming in primary CML cells derived from 38 bone marrow specimens of CML patients (TABLE 1). CML CD34+ cell isolated were separately treated with 0.25 µM imatinib, 4 µM fenretinide, or the combinations of 4 µM fenretinide with 0.25 µM imatinib, and subjected to progenitor colony forming assay, respectively for CFU-GM, BFU-E, and CFU-GEMM. As shown in FIG. 14, the co-treatment of 4 µM fenretinide and 0.25 µM imatinib could significantly reduce the number of CFU-GM and BFU-E, compared with that when treated with agents alone. Moreover, GFU-GEMM formed by the more primitive progenitor cells could be detected in the untreated and imatinib groups but not in the fenretinide and co-treated groups.

Figure 15:
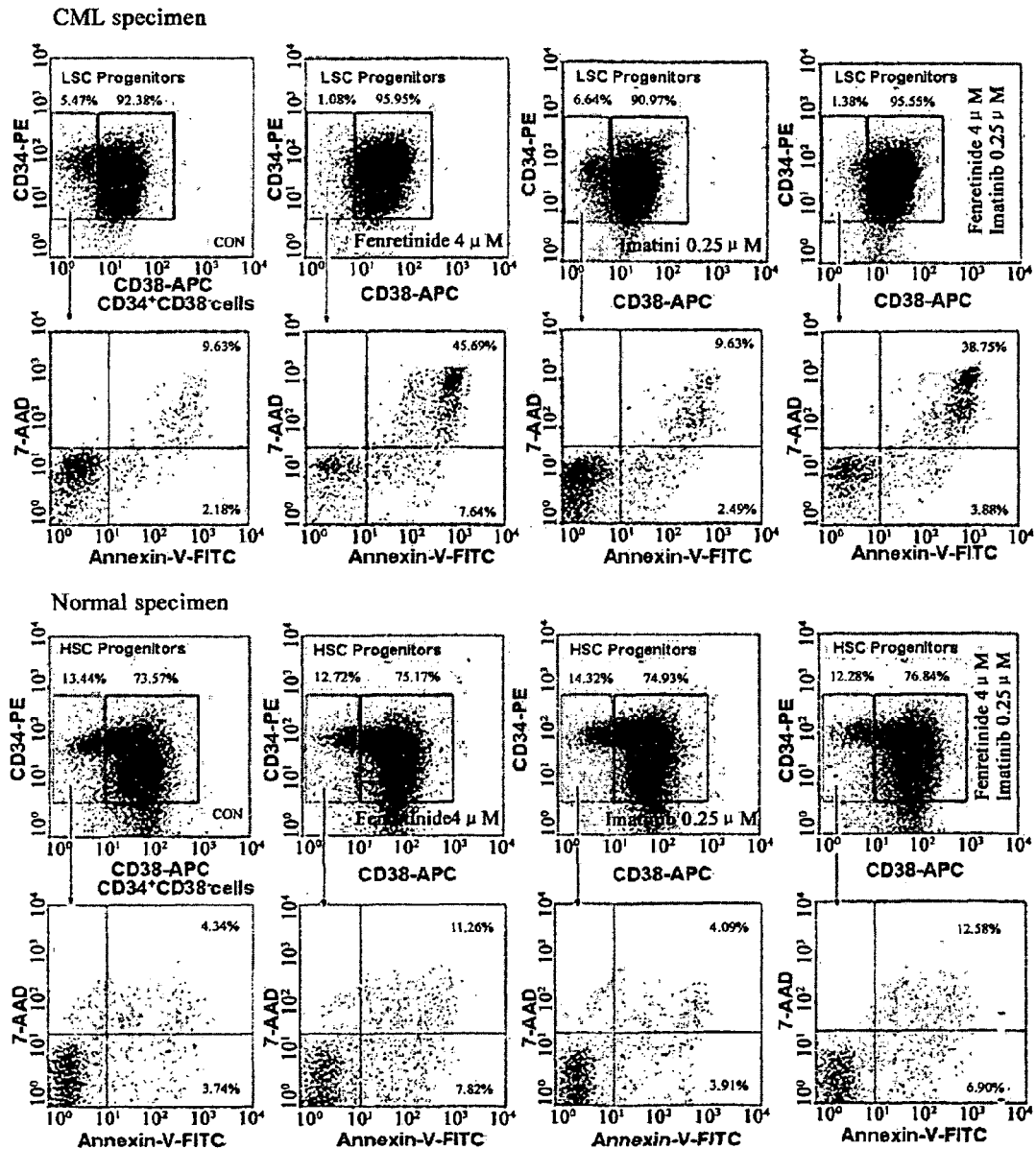
FIG. 15 shows effects of fenretinide and imatinib on CML stem and progenitor cells and normal hematopoietic stem cells. CD34-PE and CD38-APC antibodies were utilized to analyze the subpopulations of the CML cells derived from bone marrow specimens of CML patients, CD34+CD38− enriched with CML stem cells (LSC) and normal hematopoietic stem cells (HSC), and CD34+CD38+ enriched with CML progenitor cells and normal hematopoietic progenitor cells. Apoptosis rates were examined through annexin-V FITC and 7AAD double staining.

To determine whether fenretinide and imatinib have partialities on the subpopulation of the CD34+ cells, we labeled the CD34+ cells after the drug treatment with antibodies against the CD34 and CD38 markers and assessed the apoptosis by FACS. As shown in FIG. 15, The apoptosis in the CML stem cells was also significantly induced by fenretinide (53.3%) and the co-treatment (42.6%) compared to that of the untreated and imatinib treated cells (p<0.001). However, the toxicity in normal hematopoietic stem cells (HSC) induced by fenretinide and the co-treatment was extremely low with little apoptosis (19.08% and 19.48%, respectively). Based on these observations, we emphasize that the synergistic effect of fenretinide and imatinib on the primary cells mainly exhibit their ability to target different cell populations but not the merely amplified effects of the two agents on the same cell population. It is well known that imatinib can effectively target the differentiated CML cells, whereas fenretinide, first reported in our study, can especially target the CML stem cells while sparing the normal cell counterparts. Such synergistic effects provide an effective clinical therapeutic strategy to overcome imatinib resistance and the disease relapse in patients with CML.

Figure 16:
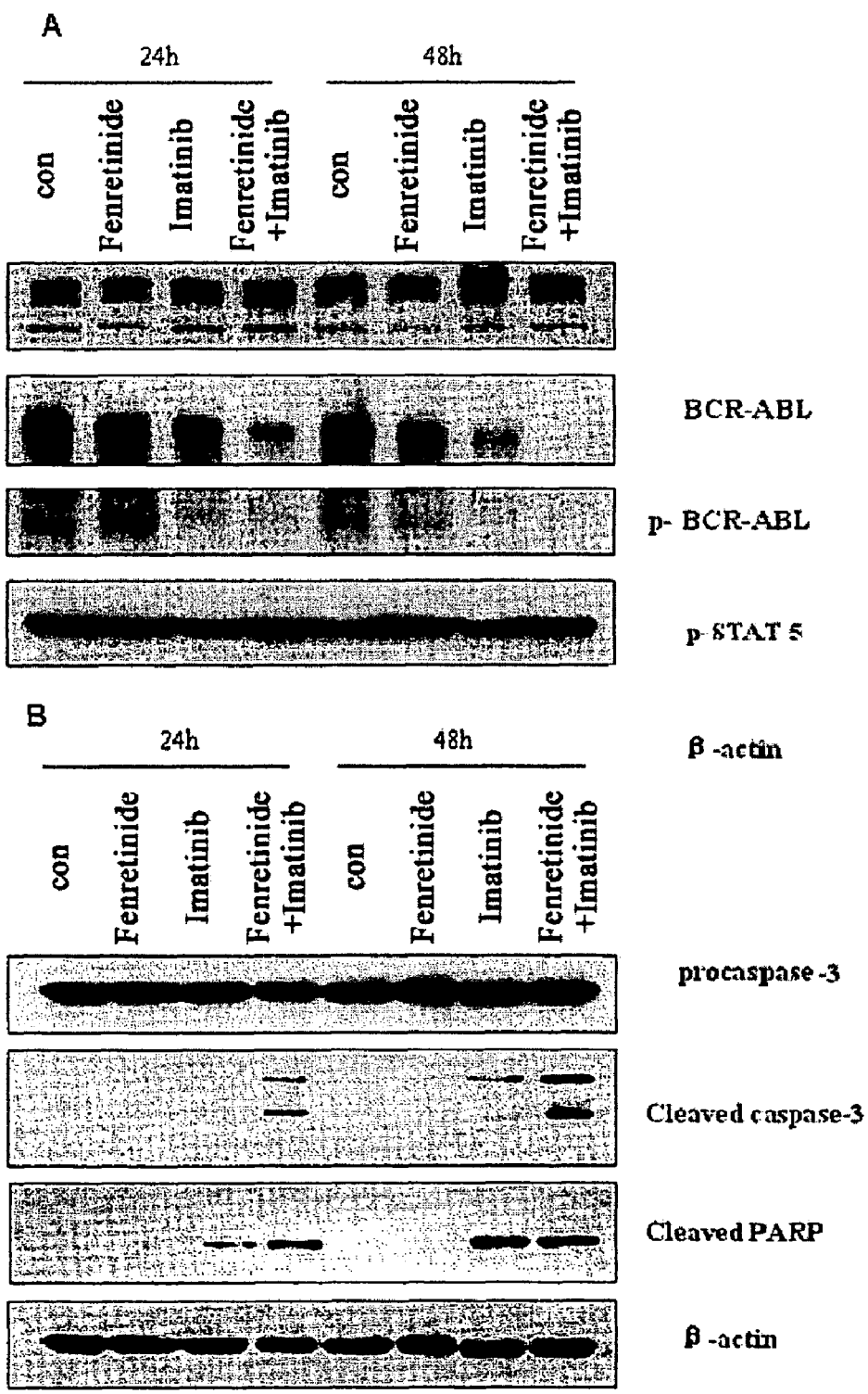
FIGS. 16A and 16B show the effects of fenretinide and imatinib on BCR-ABL activities in K562 cells. (A) The protein expression of BCR-ABL and phosphorylation levels of p-BCR-ABL and p-STAT in K562 cells treated with fenretinide, imatinib or both, as evaluated by Western Blot analysis. (B) Apoptosis markers of procaspase 3, cleaved caspase3 and cleaved PARP in K562 cells treated with fenretinide, imatinib or both, as evaluated by Western Blot analysis. CON, untreated control; H, fenretinide; S, imatinib; H+S, fenretinide+imatinib.

To get insight into the mechanism underlying the coordination effect of fenretinide and imatinib, we performed a series of Western blot analysis on K562 cells treated with fenretinide, imatinib or both with specific antibodies of BCR-ABL, phospho-BCR-ABL, phospho-STAT5, procaspase 3, cleaved caspase3 and cleaved PARP. As shown in FIG. 16A, the protein level of BCR-ABL was not changed in all of the treatments, while the phosphorylation activity of BCR-ABL was obviously reduced in the imatinib treatment with the inhibition of 50% at 24 hours and 85% at 48 hours compared to that of the untreated control. The co-treatment of the two agents extremely reduced the phosphorylation level with the inhibition of 80% at 24 hours and 99% at 48 hours. Similar was the case for the phosphorylation activities of STAT 5. Besides, the most activities of caspase 3 and PARP were cleaved by the co-treatment (FIG. 16B). Together, fenretinide and imatinib could decline more BCR-ABL activity and thus promote more cell apoptosis in the CML-derived K562 cells.

Example 11

Effects of Fenretinide, Cytosine Arabinoside and MG132 on Apoptosis in AML Cell Line U937

Figure 17:
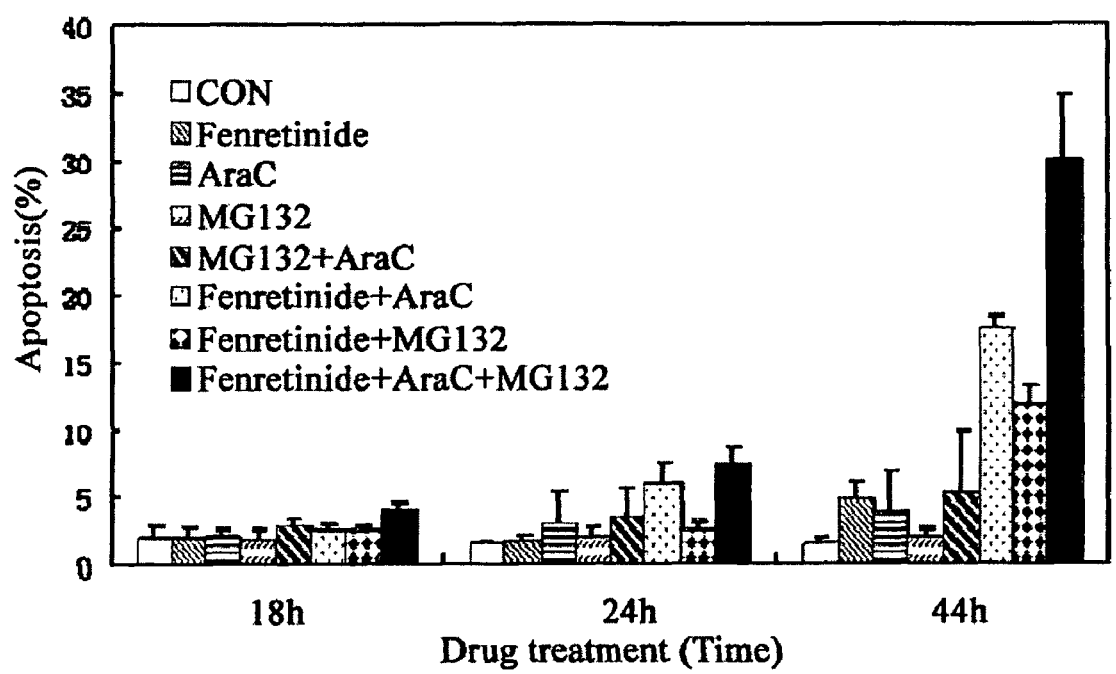
FIG. 17 shows synergistic effect of fenretinide, cytosine arabinoside and MG132 on apoptosis in AML cell line U937.

There are two observations that drive us in further exploring alternative therapeutic combinations. As illustrated in Example 6, proteasome inhibitors can potentate fenretinide-induced apoptosis in leukemia. Besides, conventional chemotherapeutic agents can exert synergistic effects on growth inhibition with fenretinide, as shown in Example 9. Here, we show synergistic effect of fenretinide, cytosine arabinoside (Ara-C) and proteasome inhibitor MG132 on apoptosis in AML cell line U937. The apoptosis rates were quite low when treated alone within 48 hours (nearly 5%), and the number doubled when treated by fenretinide and MG132. More importantly, the apoptosis induced by triple combination of fenretinide, Ara-C and MG132 was markedly enhanced, reaching as high as 35% apoptosis rate, which is significantly higher than any combination of two drugs (FIG. 17). It should be noted that the doses of Ara-C and MG132 were under the level used clinically, suggesting the potentials of lowering the toxicity.

Example 12

Synergistic Effect of Fenretinide, Imatinib and MG132 on Apoptosis in CML Cell Line K562

Figure 18:
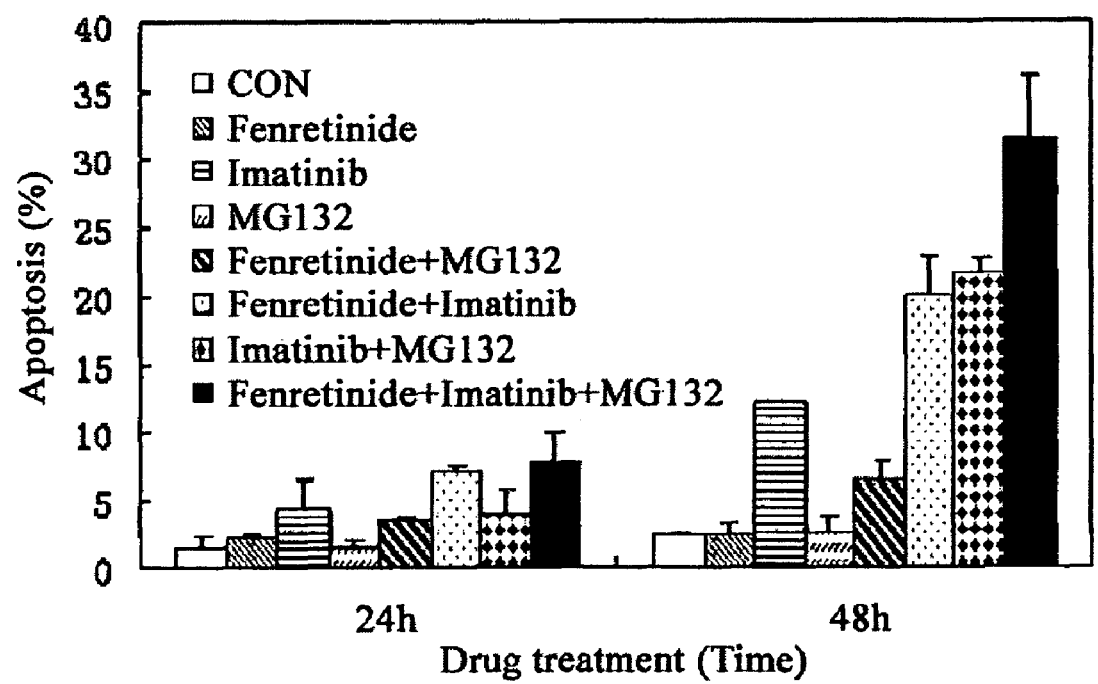
FIG. 18 shows synergistic effect of fenretinide, imatinib and MG132 on apoptosis in CML cell line K562.

In the previous case (See Example 10), we have examined the synergistic effects of fenretinide and imatinib on CML cells, and also studied the underlying synergistic mechanism. Similarly in Example 11, we explored whether proteasome inhibitor can further improve the observed synergistic effects of fenretinide and imatinib in K562. As shown in FIG. 18, apoptosis rate in triple combination (31.66%) was much higher than any dual combination (e.g., 21.04% in fenretinide/imatinib combination), not to mention single treatment (i.e., 2.46%, 12.8% and 2.51%, respectively in the mono-treatment of 4 µM fenretinide, 0.25 µM imatinib and 0.1 µM MG132). Such strategy of combining more than anti-tumor therapeutic agents with fenretinide provides a more promising opportunity for CML patients.

Example 13

Figure 19:
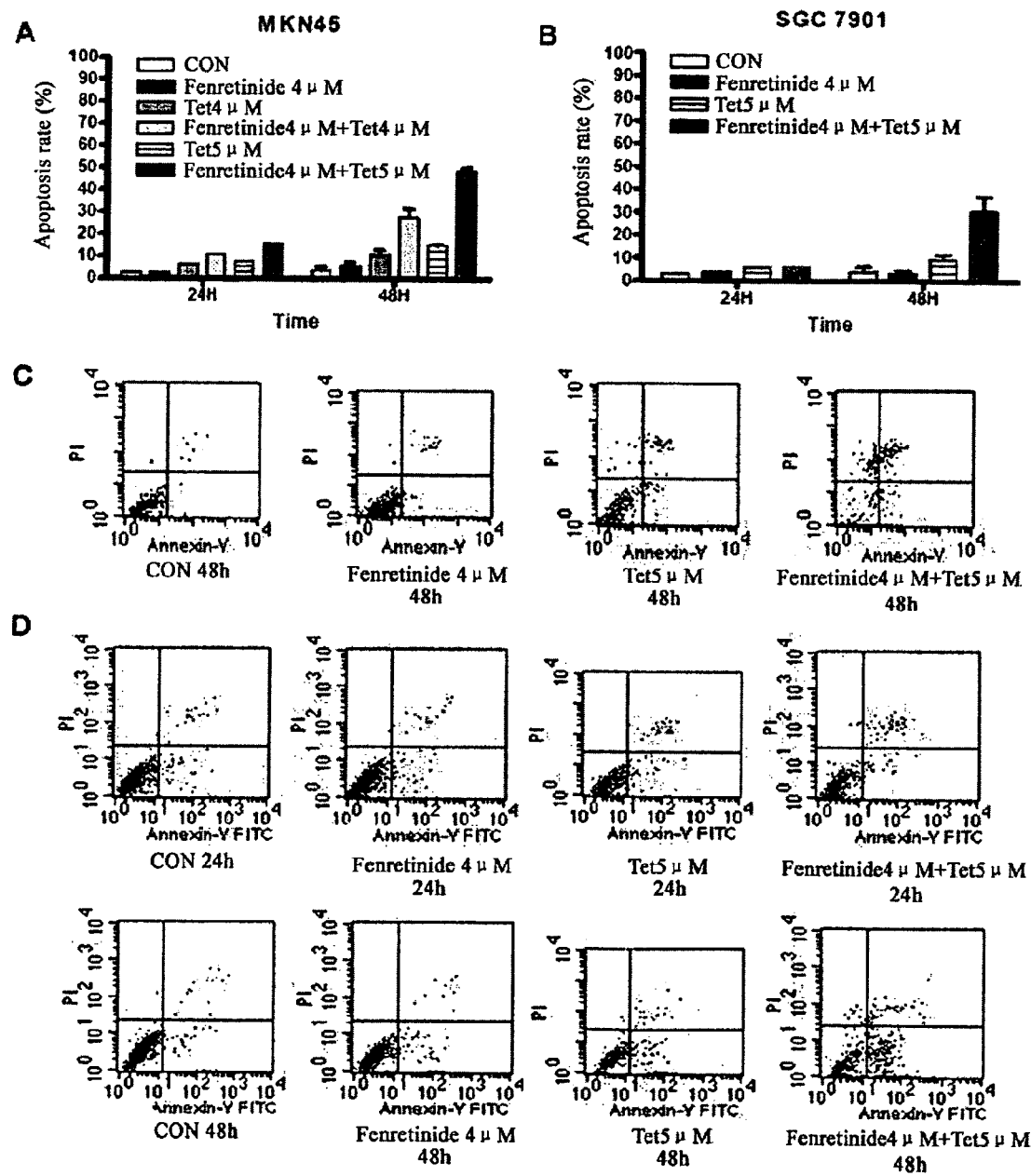
FIGS. 19A and 19B and 19C and 19D show synergistic effect of fenretinide combined with anti-cancer and anti-inflammation drug tetrandrine on apoptosis in gastric tumor cells. (A, B) Synergistic induction of apoptosis by fenretinide and tetrandrine in gastric tumor cell lines MKN45 and SGC 7901, as evaluated by Rh123/PI double stain using FACS. (C, D) Apoptosis profiles of fenretinide/tetrandrine co-treated MKN45 and SGC7901 cells, as examined through annexin-V/PI double staining.

Effects of Fenretinide Combined with Tetrandrine on Apoptosis in Gastric Tumor Cells Fenretinide induces intracellular ROS and ER stress to activate series of molecular events including apoptotic pathway and such anti-apoptotic pathways as NF-κB cascade. NF-κB can mediate the progression of inflammation-related cancer. From a wide broad of bioactive compounds, we screened tetrandrine (Tet) as a potential agent which, together with fenretinide, synergistically induced apoptosis of gastric tumor cell line. Unlike fenretinide, Tet is the well-known anti-cancer and anti-inflammation drugs via inhibiting the activity of NF-κB. For example, Tet, as the main effective component of Stephenia tetrandra S Moore, has bioactivities in reversing MDR (multidrug resistance), blocking calcium ion channel and so on. Here, we showed that 4 µM fenretinide and 4-5 µM Tet synergistically induced apoptosis on gastric tumor cell lines MKN45 and SGC7901. FIGS. 19A and 19B show synergistic induction of apoptosis by fenretinide and Tet, as evaluated by Rh123/PI double stain using FACS. Co-treatment of 4 µM fenretinide and 4 µM (or 5 µM) Tet in MKN45 cells for 48 hours induced more apoptosis than treated alone (i.e., 6.2%, 15.8% and 49.4%, respectively in the mono-treatment of 4 µM fenretinide, 5 µM Tet and co-treatment of both agents). Similarly, fenretinide and Tet had synergistic effect on apoptosis in SGC7901. Through annexin-V/PI double staining, synergistic apoptosis profiles of fenretinide/tetrandrine co-treated MKN45 and SGC7901 cells were also observed (see FIGS. 19C and 19D). Thus, the combination of fenretinide with anti-tumor agents (like Tet) can provide more effective therapeutic strategy for the solid tumor, as illustrated in gastric malignancy.

Example 14

Serum-Deprived Quiescent Leukemic Cells are More Sensitive to 4-oxo-N-(4-hydroxyphenyl)retinamide As previous case (Example 1), HL60 cells were chosen as serum deprived quiescent leukemic cell model obtained when incubated in RPMI 1640 without serum for 48 h. Serum-deprived quiescent leukemic cells and proliferating leukemic cells were then cultured in media containing 0.5% FBS, and treated with 0-10 µM 4-oxo-N-(4-hydroxyphenyl)retinamide for 24 and 48 h, respectively. The cell viability was test by MTT assay. Similar to effects exerted by fenretinide, Serum-deprived quiescent leukemic cells are more sensitive to 4-oxo-N-(4-hydroxyphenyl)retinamide, compared with proliferating HL60 cells (TABLE 3).

Example 15

4-oxo-N-(4-hydroxyphenyl)retinaniide Preferentially Targets More Primitive AML Stem and Progenitor Cells To determine whether 4-oxo-N-(4-hydroxyphenyl)retinamide like fenretinide could preferentially target primitive leukemia cells, CD34+ cells are isolated from bone marrow specimens of AML patients and subjected to apoptosis assay upon the treatment with 1-7.5 µM 4-oxo-N-(4-hydroxyphenyl)retinamide for 48 h. After gating on primitive AML subfractions by CD34-PE and CD38-APC antibodies, 4-oxo-N-(4-hydroxyphenyl) retinamide induces apoptosis of CD34+ CD38+ AML progenitor cells and the CD34+CD38− AML stem cells in a dose-dependent manner, similar to preferential target effects of fenretinide (Example 4). These results demonstrate that 4-oxo-N-(4-hydroxyphenyl)retinamide is a promising drug targeting leukemia stem and progenitor cells.

III. Preparation Example

Fenretinide Oral Preparation

| Fenretinide Oral Preparation Capsule (1000 pills, 50 mg/pill) | |
|---|---|
| Composition | Feeding amount |
| Fenretinide | 50 g |
| Lecithin | 7.5 g |
| Hydrogenated soybean oil | 7.5 g |

-continued

| Fenretinide Oral Preparation Capsule (1000 pills, 50 mg/pill) | |
|---|---|
| Composition | Feeding amount |
| Beeswax | 10 g |
| BHA (butyl hydroxyanisole) | 0.25 g |
| Vegetable oil | 214.75 g |

Preparation Process:

Water, glycerol, ethyl para-hydroxybenzoate (dissolved in an appropriate amount of over 95% medical alcohol) and gelatin are preheated to 80° C., then placed in a concentrating pan, filtered under a steam pressure not exceeding 0.06 Mpa and at a temperature of 60±2° C., then discharged. The obtained soft capsule wall is left for later use. Additionally, at a temperature below 60° C., fenretinide and BHA are added to a proper amount of vegetable oil, stirred and homogeneously mixed, and a filtered mixture of beeswax and hydrogenated soybean oil as well as the rest vegetable oil are thereafter added. After grinding of the blender, lecithin is added into, stirred and homogeneously mixed. The oily material is encapsulated in the ready-to-use soft capsule wall as prepared as above in a pill room to obtain pills. After shaping, the pills are subject to baking twice at a low temperature of 26-30° C. and 30-35° C., respectively, and both under a relative humidity≦40%, and then washed with petroleum ether for one or two times, dried, sorted, packed and sealed in a plastic package to obtain the final product.

REFERENCES CITED

| U.S. patent Documents | | |
|---|---|---|
| 4,190,594 | February 1980 | Gander et al. |
| 4,665,098 | May 1987 | Gibbs et al. |
| 5,464,870 | November 1995 | Veronesi et al. |
| 6,352,844 | March 2002 | Maurer et al. |
| 6,368,831 | April 2002 | Maurer et al. |
| 6,733,743 | May 2004 | Jordan. |
| 6,869,795 | March 2005 | Bartelmez et al. |
| 7,169,813 | January 2007 | Formelli. |
| 7,169,819 | January 2007 | Gupta et al. |

OTHER REFERENCES

1. Bonnet D, Dick J E: Human acute myeloid leukemia is organized as a hierarchy that originates from a primitive hematopoietic cell. *Nat. Med.* 1997, 3:730-737.
2. Blanpain C, Lowry W E, Geoghegan A, Polak L, Fuchs E: Self-renewal, multipotency, and the existence of two cell populations within an epithelial stem cell niche. *Cell* 2004, 118:635-648.
3. Cobaleda C, Gutierrez-Cianca N, Perez-Losada J, Flores T, Garcia-Sanz R, Gonzalez M, Sanchez-Garcia I: A primitive hematopoietic cell is the target for the leukemic transformation in human philadelphia-positive acute lymphoblastic leukemia. *Blood* 2000, 95:1007-1013.
4. Jordan C T, Guzman M L, Noble M: Cancer stem cells. *N. Engl. J. Med.* 2006, 355:1253-1261.
5. Hope K J, Jin L, Dick J E: Acute myeloid leukemia originates from a hierarchy of leukemic stem cell classes that differ in self-renewal capacity. *Nat. Immunol.* 2004, 5:738-743.

6. Lapidot T, Sirard C, Vormoor J, Murdoch B, Hoang T, Caceres-Cortes J, Minden M, Paterson B, Caligiuri M A, Dick J E: A cell initiating human acute myeloid leukaemia after transplantation into SCID mice. *Nature* 1994, 367: 645-648.
7. Huntly B J, Gilliland D G: Blasts from the past: new lessons in stem cell biology from chronic myelogenous leukemia. *Cancer Cell* 2004, 6:199-201.
8. Deininger M W, Goldman J M, Melo J V: The molecular biology of chronic myeloid leukemia. *Blood* 2000, 96:3343-3356.
9. Graham S M, Jorgensen H G, Allan E, Pearson C, Alcorn M J, Richmond L, Holyoake T L: Primitive, quiescent, Philadelphia-positive stem cells from patients with chronic myeloid leukemia are insensitive to STI571 in vitro. *Blood* 2002, 99:319-325.
10. Guan Y, Hogge D E: Proliferative status of primitive hematopoietic progenitors from patients with acute myelogenous leukemia (AML). *Leukemia* 2000, 14:2135-2141.
11. Guzman M L, Swiderski C F, Howard D S, Grimes B A, Rossi R M, Szilvassy S J, Jordan C T: Preferential induction of apoptosis for primary human leukemic stem cells. *Proc. Natl. Acad. Sci. U.S.A* 2002, 99:16220-16225.
12. Guan Y, Gerhard B, Hogge D E: Detection, isolation, and stimulation of quiescent primitive leukemic progenitor cells from patients with acute myeloid leukemia (AML). *Blood* 2003, 101:3142-3149.
13. Lynas J F, Harriott P, Healy A, McKervey M A, Walker B: Inhibitors of the chymotrypsin-like activity of proteasome based on di- and tri-peptidyl[alpha]-keto aldehydes (glyoxals). *Bioorganic & Medicinal Chemistry Letters* 1998, 8:373-378.
14. Xiao L, Wang K, Teng Y, Zhang J: Component plane presentation integrated self-organizing map for microarray data analysis. *FEBS Lett.* 2003, 538:117-124.
15. Bello R I, Gomez-Diaz C, Lopez-Lluch G, Forthoffer N, Cordoba-Pedregosa M C, Navas P, Villalba J M: Dicoumarol relieves serum withdrawal-induced G0/1 blockade in HL-60 cells through a superoxide-dependent mechanism. *Biochem. Pharmacol.* 2005, 69:1613-1625.
16. Sun S Y, Li W, Yue P, Lippman S M, Hong W K, Lotan R: Mediation of N-(4-hydoxyphenyl)retinamide-induced apoptosis in human cancer cells by different mechanisms. *Cancer Res.* 1999, 59:2493-2498.
17. Oridate N, Suzuki S, Higuchi M, Mitchell M F, Hong W K, Lotan R: Involvement of reactive oxygen species in N-(4-hydroxyphenyl)retinamide-induced apoptosis in cervical carcinoma cells. *J. Natl. Cancer Inst.* 1997, 89:1191-1198.
18. Jaiswal A K: Nrf2 signaling in coordinated activation of antioxidant gene expression. *Free Radic. Biol. Med.* 2004, 36:1199-1207.
19. D'Autreaux B, Toledano M B: ROS as signalling molecules: mechanisms that generate specificity in ROS homeostasis. *Nat. Rev. Mol. Cell Biol.* 2007, 8:813-824.
20. Hayashida N, Inouye S, Fujimoto M, Tanaka Y, Izu H, Takaki E, Ichikawa H, Rho J, Nakai A: A novel HSF1-mediated death pathway that is suppressed by heat shock proteins. *EMBO J.* 2006,25:4773-4783.
21. Ahn S G, Thiele D J: Redox regulation of mammalian heat shock factor 1 is essential for Hsp gene activation and protection from stress. *Genes Dev.* 2003, 17:516-528.
22. Zheng P Z, Wang K K, Zhang Q Y, Huang Q H, Du Y Z, Zhang Q H, Xiao D K, Shen S H, Imbeaud S, Eveno E, Zhao C J, Chen Y L, Fan H Y, Waxman S, Auffray C, Jin G, Chen S J, Chen Z, Zhang J: Systems analysis of transcriptome and proteome in retinoic acid/arsenic trioxide-induced cell differentiation/apoptosis of promyelocytic leukemia. *Proc. Natl. Acad. Sci. U.S.A* 2005, 102:7653-7658.
23. Murray J I, Whitfield M L, Trinklein N D, Myers R M, Brown P O, Botstein D: Diverse and specific gene expression responses to stresses in cultured human cells. *Mol. Biol. Cell* 2004, 15:2361-2374.
24. Meusser B, Hirsch C, Jarosch E, Sommer T: ERAD: the long road to destruction. *Nat. Cell Biol.* 2005, 7:766-772.
25. Druker B J, Guilhot F, O'Brien S G, Gathmann I, Kantarjian H, Gattermann N, Deininger M W, Silver R T, Goldman J M, Stone R M, Cervantes F, Hochhaus A, Powell B L, Gabrilove J L, Rousselot P, Reiffers J, Cornelissen J J, Hughes T, Agis H, Fischer T, Verhoef G, Shepherd J, Saglio G, Gratwohl A, Nielsen J L, Radich J P, Simonsson B, Taylor K, Baccarani M, So C, Letvak L, Larson R A: Five-year follow-up of patients receiving imatinib for chronic myeloid leukemia. *N. Engl. J. Med.* 2006, 355: 2408-2417.
26. Shah N P, Nicoll J M, Nagar B, Gorre M E, Paquette R L, Kuriyan J, Sawyers C L: Multiple BCR-ABL kinase domain mutations confer polyclonal resistance to the tyrosine kinase inhibitor imatinib (ST1571) in chronic phase and blast crisis chronic myeloid leukemia. *Cancer Cell* 2002, 2:117-125.

What is claimed is:

1. A pharmaceutical composition comprising a therapeutically effective amount of fenretinide or a bioactive derivative thereof, a therapeutically effective amount of at least one additional anti-tumor agent, and, optionally, a pharmaceutically acceptable carrier, wherein said at least one additional anti-tumor agent is to be administered simultaneously, sequentially or separately with fenretinide or bioactive derivatives thereof to synergistically induce apoptosis of tumor stem cells in the subject.

2. The composition according to claim 1, wherein said additional anti-tumor agent is selected from the group consisting of cell cycle-specific chemotherapeutic agents, BCR-ABL tyrosine kinase-targeted inhibitors, proteasome inhibitors, and conventional chemotherapeutic agents having different action mechanism with the cell cycle-specific chemotherapeutic agents, BCR-ABL tyrosine kinase-targeted inhibitors, and proteasome inhibitors.

3. The composition according to claim 2, wherein said cell cycle-specific chemotherapeutic agent is selected from the group consisting of arabinoside, 5-fluorouracil, hydroxyurea, 6-mercaptopurine, 6-thioguanine, fludarabine, and methotrexate.

4. The composition according to claim 2, wherein said BCR-ABL tyrosine kinase-targeted inhibitor is selected from the group consisting of imatinib, dasatinib, and nilotinib.

5. The composition according to claim 2, wherein said proteasome inhibitor is selected from the group consisting of bortezomib, BzLLLCOCHO, and MG-132.

6. The composition according to claim 2, wherein said conventional chemotherapeutic agent having different action mechanism with the cell cycle-specific chemotherapeutic agents, BCR-ABL tyrosine kinase-targeted inhibitors, and proteasome inhibitors is selected from the group consisting of idarubicin, vincristine, doxorubicin, daunorubicin, mitoxantrone, vinblastine, vindesin, harringtonine, etoposide, teniposide, L-asparaginase, cyclophosphamide, and cisplatin.

7. The composition according to claim 1, wherein the bioactive derivative of fenretinide is 4-oxo-N-(4-hydroxyphenyl) retinamide.

8. A method of killing tumor stem cells therefrom in a subject, comprising administering fenretinide or a bioactive derivative thereof in an amount effective to induce apoptosis of tumor stem cells.

9. The method of claim 8, further comprising administering a therapeutically effective amount of at least one additional anti-tumor agent, wherein said at least one additional anti-tumor agent is to be administered simultaneously, sequentially, or separately with fenretinide or a bioactive derivative thereof to synergistically induce apoptosis of tumor stem cells in the subject.

10. The method according to claim 9, wherein the tumor is a hematologic tumor.

11. The method according to claim 10, wherein said hematologic tumor is selected from the group consisting of leukemia and malignant lymphoproliferative disorders.

12. The method according to claim 11, wherein said leukemia is selected from the group consisting of acute myelogenous leukemia, chronic myelogenous leukemia, myelodysplastic syndrome, acute lymphoid leukemia and chronic lymphoid leukemia, and said malignant lymphoproliferative disorder is selected from the group consisting of lymphoma and multiple myeloma.

13. The method according to claim 12, wherein said lymphoma is selected from the group consisting of non-Hodgkin's lymphoma, Burkitt's lymphoma, and small cell and/or large cell follicular lymphoma.

14. The method according to claim 9, wherein said additional anti-tumor agent is selected from the group consisting of cell cycle-specific chemotherapeutic agents, BCR-ABL tyrosine kinase-targeted inhibitors, proteasome inhibitors, and conventional chemotherapeutic agents having different action mechanism with the cell cycle-specific chemotherapeutic agents, BCR-ABL tyrosine kinase-targeted inhibitors, proteasome inhibitors.

15. The method according to claim 14, wherein said cell cycle-specific chemotherapeutic agent is selected from the group consisting of arabinoside, 5-fluorouracil, hydroxyurea, 6-mercaptopurine, 6-thioguanine, fludarabine, and methotrexate.

16. The method according to claim 14, wherein said proteasome inhibitor is selected from the group consisting of bortezomib, BzLLLCOCHO, and MG-132.

17. The method according to claim 14, wherein said conventional chemotherapeutic agent having different action mechanism with the cell cycle-specific chomotherapeutic agents, BCR-ABL tyrosine kinase-targeted inhibitors, proteasome inhibitors is selected from the group consisting of idarubicin, vincristine, doxorubicin, daunorubicin, mitoxantrone, vinblastine, vindesin, harringtonine, etoposide, teniposide, L-asparaginase, cyclophosphamide, and cisplatin.

18. The method according to claim 8, wherein the bioactive derivative of fenretinide is 4-oxo-N-(4-hydroxyphenyl) retinamide.

19. The method according to claim 8, wherein the tumor is a solid tumor.

20. The method according to claim 8, wherein said additional anti-tumor agent is a BCR-ABL tyrosine kinase-targeted inhibitor.

21. The method according to claim 19, wherein said solid tumor is selected from the group consisting of gastric cancer, lung cancer, ovarian cancer and neuroblastoma.

22. The method according to claim 20, wherein said BCR-ABL tyrosine kinase-targeted inhibitor is selected from the group consisting of imatinib, dasatinib, and nilotinib.

* * * * *

UNITED STATES PATENT AND TRADEMARK OFFICE
CERTIFICATE OF CORRECTION

PATENT NO. : 8,088,822 B2
APPLICATION NO. : 12/169532
DATED : January 3, 2012
INVENTOR(S) : Ji Zhang and KanKan Wang It is certified that error appears in the above-identified patent and that said Letters Patent is hereby corrected as shown below:

Column 13,
Line 59, "$CD34^+$ Cell were" should read --$CD34^+$ cells were--.
Line 63, "samples detennined by" should read --samples determined by--.

Column 14,
Line 15, "BD Phanningen, San Diego" should read --BD Pharmingen, San Diego--.
Lines 46-47, "BD Phanningen, San Diego" should read --BD Pharmingen, San Diego--.

Column 15,
Lines 20-21, "CDNA clones" should read --cDNA clones--.

Column 16,
Line 66, "isolated using using" should read --isolated using--.

Column 17,
Line 12, "36±9%" should read --36%±9%--.
Line 28, "Upon treated" should read --Upon being treated--.
Line 37, "CD34+CD38-" should read --$CD34^+CD38^-$--.
Line 56, "with sparing" should read --while sparing--.

Column 18,
Line 18, "relative resistant" should read --relatively resistant--.
Line 36, "should below" should read --should be below--.
Line 37, "specifically target" should read --specifically to target--.
Line 44, "from $CD34^-$" should read --from $CD34^+$--.
Line 59, "Fenretinide induces" should read --Fenretinide-induced--.

Column 19,
Line 3, "descend manner" should read --descending manner--.

Signed and Sealed this
Third Day of April, 2012

David J. Kappos
*Director of the United States Patent and Trademark Office*

CERTIFICATE OF CORRECTION (continued)
U.S. Pat. No. 8,088,822 B2

Line 59, "of there two" should read --of these two--.

Column 20,
Line 45, "we comparatively these" should read --we compared these--.

Column 25,
Line 37, "4-oxo-N-(4-hydroxyphenyl)retinaniide" should read
--4-oxo-N-(4-hydroxyphenyl)retinamide--.
Lines 55-57, "III. Preparation Example Fenretinide Oral Preparation" should read --III. Preparation Example--.

Column 26,
Line 21, "the rest vegetable oil" should read --the rest of the vegetable oil--.
Line 28, "$\leqq 40\%$" should read --$\leq 40\%$--.

Column 27,
Lines 12-13, "Alcom MJ" should read --Alcorn MJ--.

Column 28,
Line 12, "Comelissen J J" should read --Cornelissen JJ--.

Column 29,
Line 1, "stem cells therefrom in a" should read --stem cells in a--.